(12) United States Patent
Goldstein et al.

(10) Patent No.: US 6,563,014 B2
(45) Date of Patent: May 13, 2003

(54) SELF-CONTAINED SYSTEM FOR SUSTAINED VIRAL REPLICATION

(75) Inventors: Harris Goldstein, Teaneck, NJ (US); Jessie Browning Paul, New York, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 09/460,555

(22) Filed: Dec. 14, 1999

(65) Prior Publication Data

US 2002/0013952 A1 Jan. 31, 2002

(51) Int. Cl.⁷ ..................... A01K 67/027; A01K 67/00; A01K 67/033; G01N 33/00
(52) U.S. Cl. ................ 800/3; 800/18; 800/8; 800/9; 800/11
(58) Field of Search ............... 800/8, 11, 13, 800/18, 22, 23, 25, 3, 9

(56) References Cited

FOREIGN PATENT DOCUMENTS

WO        WO 98/58536     *  6/1998  ......... A01K/67/027

OTHER PUBLICATIONS

Browning et al, 1997, PNAS, 94: 14637–14641.*
Ebert et al, 1988, Mol. Endocrinol., 2: 277–283.*
Hammer et al, 1986, J. Anim. Sci., 63: 269–278.*
Houdebine et al, 1994, J. Biotechnol., 34: 269–287.*
Kappel et al, 1992, Cur. Opin. Biotechnol., 3: 548–553.*
Moore et al, 1997, Cur. Opin Immunol., 9: 551–562.*
Mullins et al, 1996, J. Clin Invest., 98: S37–S40.*
Strojek et al, 1988, Genetic Engineering: Prin. and Meth., 10: 221–246.*
Wall et al, 1996, Theriogenology, 45: 57–68.*
Dickie et al, 1996, AIDS Res. Hu. Retro., 12: 1103–1116.*
JJ Mullins et al., EMBO Journal, "Expression of the DBA/aJ Ren–2 gene in the adrenal gland of transgenic mice," 1989, vol. 8, No. 13, pp. 4065–4072.*
JJ Mullins et al., Nature, "Fulminant hypertension in transgenic rats harbouring the mouse Ren–2 gene," Apr. 1990, vol. 344, pp. 541–544.*
RE Hammer et al., Cell, "Spontaneous Inflammatory Disease in Transgenic Rats Expressing HLA–B27 and Human Beta2m:An Animal Model of HLA–B27–Associated Human Disorders," Nov. 1990, vol. 63, pp. 1099–1112.*
JD Taurog et al., Journal of Immunology, "HLA–B27 in Inbred and Non–Inbred Transgenic Mice," Dec. 1988, vol. 141, No. 11, pp. 4020–4023.*
Jon Cohen, Science—News Focus article entitled "Building a Small–Animal Model For AIDS, Block by Block," Aug. 10, 2001, vol. 293, pp. 1034–1036.

* cited by examiner

Primary Examiner—Scott D. Priebe
Assistant Examiner—Peter Paras, Jr.
(74) Attorney, Agent, or Firm—Amster, Rothstein & Ebenstein

(57) ABSTRACT

Transgenic non-human animals are described comprising a transgene for a species-specific pathogen and transgene(s) for at least one receptor restricting infection of the pathogen to the host species. Also described is a method for creating the transgenic non-human animal of this invention and a method for screening an agent for the ability to inhibit infection by a species-specific virus using said transgenic non-human animal. The transgenic animal of this invention has a sustained productive viral infection and does not develop a virus-specific immune response, thereby resulting in an extremely useful self-contained system to investigate the factors modulating in vivo replication of human pathogens, the pathophysiological effect of pathogen replication and production, and the effectiveness of novel therapies and vaccines modifying or inhibiting the course of pathogenesis.

2 Claims, 19 Drawing Sheets

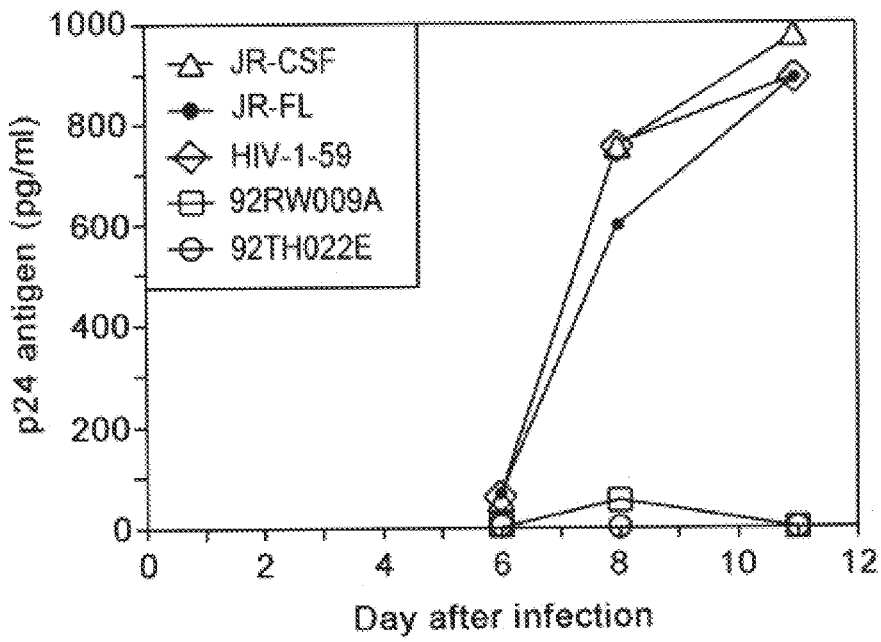
FIG. 5A
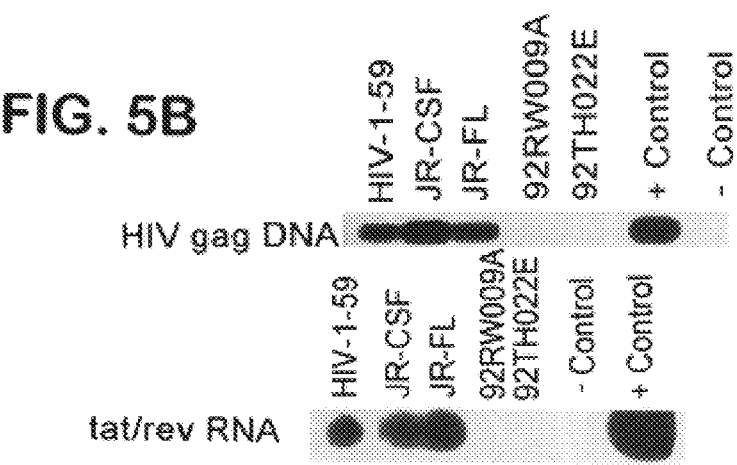
FIG. 5B
FIG. 5C

SELF-CONTAINED SYSTEM FOR SUSTAINED VIRAL REPLICATION

STATEMENT OF GOVERNMENT INTEREST

This invention was made with government support under NIH Grant No. AI 42621. As such, the government has certain rights in this invention.

FIELD OF THE INVENTION

This invention is directed to the development of an animal model to study infection by species-specific pathogens having a limited host range, preferably human-specific pathogens where the limited host range includes humans, comprised of crossing an animal transgenic for the pathogen with an animal transgenic for the tissue-specific expression of species-specific receptor(s) of the pathogen that restrict infection to the cells of the host species. For example, where the human-specific pathogen is a virus, the animal resulting from such a cross is transgenic both for the infectious provirus and for the human receptor or co-receptors that restrict infection to human cells. Accordingly, the transgenic animal of this invention has a sustained productive viral infection and does not develop a virus-specific immune response, thereby resulting in an extremely useful model to investigate the factors modulating in vivo replication of human pathogens, the pathophysiological effect of pathogen replication and production, and the effectiveness of novel therapies and vaccines modifying or inhibiting the course of pathogenesis.

BACKGROUND OF THE INVENTION

The development of therapeutic agents for human use is extremely expensive and time intensive. For many human diseases, the therapeutic drug and vaccine development processes have been greatly facilitated by the development of animal models that mimic or approximate human pathophysiological disease processes as well as normal human physiological processes. However, many human diseases are caused by human-specific pathogens that infect only human cells. For example, human immunodeficiency virus type 1(HIV-1), the causative agent of AIDS, can only be propagated in cells from humans and certain primates, such as chimpanzees. Since humans cannot be studied in a systematic fashion, and chimpanzees are on the endangered species list and are difficult and costly to maintain in a laboratory setting, there are no available animal models that mimic the human pathophysiological disease process of AIDS.

A pathogen, such as a virus, may be species-specific if initial infection into host cells is mediated by the interaction of species-specific receptors on the cell surface with the pathogen. There may be other barriers to productive infection in a non-host species, such as regulatory blocks preventing efficient viral replication even after initial infection into the cell. HIV-1 entry into human cells is mediated by CD4 acting in concert with one of several members of the chemokine receptor superfamily such as CXCR4 in the case of T-tropic strains of HIV-1 and CCR5 in the case of M-tropic strains of HIV-1. Mice, commonly used as animal models for human disease, are not infectible with HIV-1 because HIV-1 penetration into mouse cells is prevented by the inability of the envelope protein, gp120, to bind to the mouse homologues of these human receptor molecules (Atchison, R. E., et al., Nature 274:1924–1926, 1996). This inability of HIV to enter murine cells means that HIV cannot initially attach and enter the cells in order to replicate, nor can HIV reinfect cells to maintain a productive HIV infection.

Two basic approaches have been used to bypass the limited host range of HIV, although neither approach has been entirely satisfactory. One approach used has been to introduce a full-length infectious HIV provirus into the germ line of mice as a transgene (Klotman P. E., et al., *Curr. Top. Microbiol. Immunol.* 206:197–222, 1996). The infectious proviral clone used to construct these transgenic mice, NL4-3, was a hybrid construct that was derived by fusing the 5' half of proviral DNA from the NY5 isolate with the 3' half of proviral DNA from the LAV isolate of HIV (Adachi A., et al., *J. Virol.* 59:284–291, 1986). The initial description of these transgenic mice reported that the PBMCs of seven founder mice that transmitted intact copies of the HIV proviral DNA to their progeny did not produce infectious HIV, limiting their usefulness as an in vivo system for studying the pathophysiology of HIV infection (Leonard J. M., et al., *Science* 242:1665–1670, 1988). However, HIV could be recovered by coculture from the skin, spleen and lymph nodes of the progeny of one founder mouse and these mice displayed a phenotype of growth failure and lymphoid hyperplasia and died within a month of birth. Another group used the full-length NL4-3 provirus to produce six transgenic mouse lines and, although HIV RNA was not detected in their tissues by Northern blot analysis, their macrophages contained low levels of HIV RNA that could be increased by in vitro treatment with macrophage activators (Dickie P., et al., *AIDS Res. Hum. Recro.* 12:1103–1116, 1996).

In an attempt to increase HIV gene expression in mice transgenic for the NL4-3 construct, different heterologous promoter/enhancer sequences with increased transcriptional activity in mouse cells were introduced into the NL4-3 vector. Transgenic mice constructed using a NL4-3 proviral construct where two NFKB binding sites in the. NL4-3 LTR were replaced with two copies of the murine leukemia virus core enhancer displayed increased HIV RNA expression in lymph nodes, spleen and muscle (Dickie, P., et al., *J. Acquir. Immune Defic. Syndr. Hum. Retrovirol.* 13:101–116, 1996). Infectious HIV-1 could be isolated from their splenocytes and several lines of evidence indicated that this virus was produced by B cells (Dickie P., et al., *AIDS Res. Hum. Recro.* 12:1103–1116, 1996; Dickie, P., et al., *J. Acquir. Immune Defic. Syndr. Hum. Retrovirol.* 13:101–116, 1996). Increased HIV gene expression was also observed in transgenic mice generated with constructs where the NL4-3 vector was placed under the transcriptional control of either the mouse mammary tumor virus promoter (Jolicoeur, P., et al., *J. Virol.* 66:3904–3908, 1992) or the CD4 gene enhancer/promoter (Hanna Z., et al., *J. Virol.*72:121–132, 1998). However, these mice do not produce infectious HIV virions due to the engineered deletion of the 3'-end LTR in the construct. Other attempts using non-infectious constructs included the construction of transgenic mice using HIV-1 deletion mutants such as the NL4-3Δgag/pol construct (Dickie, P., et al., *Virology* 185:109–119, 1991), or mice transgenic for individual HIV genes such as env placed under the control of a tissue-specific promoter (Berrada, F., et al., *J. Virol.* 69:6770–6778, 1995). Although many of these mice displayed pathological changes that were associated with transgene expression, the alterations introduced into the regulation of viral gene expression may have compromised the physiological relevance of these transgenic mice to HIV-1-infected individuals. Furthermore, even in transgenic mice described above that produce infections, the virus encoded by the HIV-1 provirus cannot reinfect cells in these mice because of the inability of HIV-1 to attach and enter mouse cells, thereby rendering such a model useless for studying factors that inhibit sustained productive HIV infection.

Another approach involves the development of transgenic mice which are transgenic for the HIV-1 co-receptors required for initial entry of the virus into cell. (Browning, et al., *Proc. Natl. Acad. Sci. USA* 94:14637–14641, 1997). Peripheral blood mononuclear cells and splenocytes isolated from mice transgenic for human CD4 and CCR5 (hu-CD4/CCR5 TG mice) expressed human CD4 and CCR5 and were infectible with selected M-tropic HIV isolates. After in vivo inoculation, HIV-infected cells were detected by DNA PCR in the spleen and lymph nodes of these transgenic mice, but HIV could not be cultured from these cells despite repeated inoculations with high doses of HIV-1. This indicated that although transgenic expression of human CD4 and CCR5 permitted attachment and entry of HIV into mouse cells, sustained HIV infection was prevented by other blocks to HIV replication present in the mouse cells and/or development of an HIV-specific immune response that was rapidly eliminating HIV infected cells. This significantly limited the usefulness of this model for studying HIV-1 infection.

Another limitation of previously described models is that all of the mice transgenic for proviral HIV-1 described above were generated using proviral DNA constructs derived from T-cell line tropic, laboratory-adapted HIV-1 isolates (Klotman P. E., et al., *Curr Top. Microbiol. Immunol.* 206:197–222, 1996). The terms "T-cell line tropic" and "monocyte-tropic" refer to the restricted capacity of various HIV-1 isolates to infect T cell lines and monocytes, respectively. T-cell line tropic isolates are capable of infecting T cell lines but not monocytes, and monocyte-tropic isolates are able to infect monocytes/macrophages but not T cell lines. (Schuitemaker, H., et al., *J. Virol.* 66:1354–1360, 1991). The basis for such divergent cellular tropism is due to the fact that T-cell tropic lines of HIV-1 must interact, after binding to CD4, with CXCR4 (Feng, Y., et al., *Science* 272:872–877, 1996), while monocyte-tropic isolates utilize CCR5 as a coreceptor (Berger, E. A., et al., *AIDS* 11:53–516, 1997; Deng, H., et al., *Nature* 381, 661–667, 1996; Dragic, T., et al., *Nature* 381:667–673, 1996; Choe, H., et al., *Cell* 85:1135–1148, 1996; Alkhatib, G., et al., *Science* 272:1955–1958, 1996).

Monocyte-tropic HIV-1 strains are the primary isolate detected in individuals during the initial stages of HIV infection (Schuitemaker, H., et al., *J. Virol.* 66:1354–1360, 1992; Mosier, D., et al., *Immunol. Today* 15:332–339, 1994), and a large body of the literature suggests that M-tropic HIV-1 isolates are important in the initial establishment of infection (e.g., Van't Wout A. B., et al., *J. Clin. Invest* 94:2060–2067, 1994), a suggestion further bolstered by the demonstration that individuals homozygous for a 32 base pair deletion in the CCR5 gene do not become infected with HIV despite multiple exposures to M-tropic and T-cell line tropic HIV-1 and that their mononuclear cells are resistant to in vitro HIV infection (Liu, R., et al., *Cell* 86:367–377, 1996; Samson, M., et al., *Nature* 382:722–725, 1996). Thus, investigation of the in vivo behavior of M-tropic HIV-1 isolates is critical for understanding of the pathophysiology of HIV-1 infection.

Accordingly, there is a need to develop an animal model to study infection by human-specific or species-specific pathogens, where such a model maintains a productive viral infection and does not develop a virus-specific immune response.

SUMMARY OF THE INVENTION

The invention is directed to the development of animal models to study infection by species-specific pathogens, including infection by human-specific pathogens such as HIV or hepatitis. As such, the invention provides a self-contained system for examining sustained pathogen replication. The invention will allow researchers to use convenient and well studied small laboratory animals, including rats or mice, to study infection by pathogens having limited host ranges not normally including the selected laboratory animal, and to evaluate vaccines against such pathogens and therapeutics directed to diseases caused by or associated with such pathogens. Where the pathogen is "human-specific", the limited host range includes (or may be limited exclusively to) humans but excludes the selected laboratory animal. Where the pathogen is "species-specific", the limited host-range includes (or may be limited exclusively to) a particular species but excludes the selected laboratory animal.

Accordingly, the present invention provides for a transgenic non-human animal comprising a transgene for a species-specific pathogen and a transgene for at least one receptor restricting infection of the pathogen to a member of the host species. In addition, the invention provides a method for creating a transgenic non-human animal, comprising the steps of (i) isolating a fertilized oocyte from a female non-human donor animal; (ii) transferring a transgene for a species-specific pathogen into the fertilized oocyte; (iii) transferring the fertilized oocyte comprising the transgene for a species-specific pathogen into the uterus of a female non-human surrogate animal; (iv) maintaining said female non-human surrogate animal such that said female non-human surrogate animal gives birth to a transgenic non-human animal derived from the fertilized oocyte wherein said transgenic non-human animal comprises the transgene for the species-specific pathogen; (v) isolating a fertilized oocyte from a second female non-human donor animal; (vi) transferring at least one transgene for a receptor restricting infection of the pathogen to the host species into the fertilized oocyte; (vii) transferring the fertilized oocyte containing at least one transgene for a receptor restricting infection of the pathogen to the host species into the uterus of a second female non-human surrogate animal; (viii) maintaining said second female non-human surrogate animal such that said second female non-human surrogate animal gives birth to a transgenic non-human animal derived from the fertilized oocyte wherein said transgenic non-human animal comprises at least one transgene for a receptor restricting infection of the pathogen to the host species; and (ix) crossing the transgenic non-human animal comprising the transgene for the species-specific pathogen with the transgenic non-human animal comprising at least one transgene for a receptor restricting infection of the pathogen to the host species, such that the cross produces a transgenic non-human animal comprising a transgene for the species-specific pathogen and at least one transgene for a receptor restricting infection of the pathogen to the host species. The present invention provides that the host species may be human, such that the resulting cross produces a transgenic non-human animal comprising a transgene for a human-specific pathogen and at least one transgene for a receptor restricting infection of the pathogen to humans.

Also provided by the present invention is a method for screening an agent for the ability to inhibit infection by a species-specific virus, comprising administering the agent to be screened to a non-human animal comprising a transgene for a species-specific pathogen and a transgene for at least one receptor restricting infection of the pathogen to the host species, assaying viral levels of the transgenic animal before and after administration of the agent being screened, and analyzing the effect of the administered agent on the viral levels of the transgenic animal. The host species may be human. The invention further provides for an agent identified by the above method, where said agent is a peptide, protein, nucleic acid, ribonucleic acid, antisense RNA, antibody, drug or compound. Additional objects of the present invention will be apparent from the description which follows.

BRIEF DESCRIPTION OF THE FIGURES

The above brief description, as well as further objects and features of the present invention, will be more fully understood by reference to the following detailed description of the presently preferred, albeit illustrative, embodiments of the present invention when taken in conjunction with the accompanying figures, wherein:

FIGS. 5(A–C) depicts the HIV infection of splenocytes from a hu-CD4/CCR5 transgenic mouse. Splenocytes from founder mouse 18 were isolated, cultured in 24-well plates ($1\times10^6$ per well) in the presence of IL-2 (50 units/ml) and infected with the indicated isolates at a multiplicity of infection of about 0.004 (p24 antigen concentration of 3,465 pg, 2,993 pg, 4,394 pg, 3,704 pg, and 3,384 pg for the JR-CSF, JR-FL, HIV-159, 92RW009A and 92TH022E isolates, respectively). After 6 days of culture, all of the medium was removed and the cells were washed three times and fed with fresh medium containing IL-2. (A). At the designated time points, cleared supernatant was harvested and analyzed for the presence of p24 antigen. After two weeks of culture, the splenocytes were evaluated for the presence of gag DNA (B) and tat/rev RNA (C) by PCR.

DETAILED DESCRIPTION OF THE INVENTION

Figure 1A:
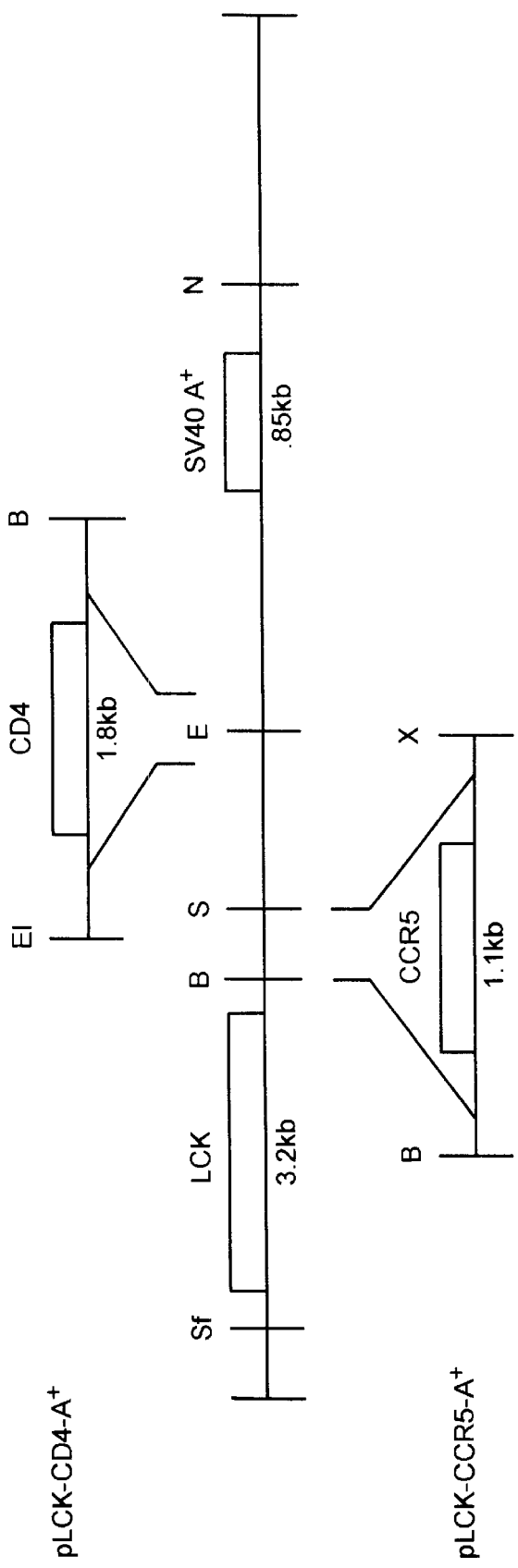
FIG. 1A sets forth the constructs used to generate human CD4/CCR5 transgenic mice. Human CD4 or CCR5 was cloned into the transgene under the control of the lck proximal promoter as shown. Restriction enzyme sites shown are: SfiI (Sf), BamHI (B), SalI (S), EcoRV (E), NotI (N), XhoI (X), and EcoRI (EI).

The present invention provides a self-contained system for examining sustained pathogen replication, where animals previously resistant to a pathogen are rendered susceptible to infection and spontaneously produce the pathogen to display self-supporting infection. Specifically, the invention provides a transgenic non-human animal comprising a transgene for a species-specific pathogen and a transgene for at least one receptor restricting infection of the pathogen to the host species. Specifically, the non-human animal can be any suitable animal, but is preferably a rodent and more preferably a rat or a mouse. In a preferred form of the invention, the species-specific pathogen is a human-specific pathogen and the host species is human, although it can be readily appreciated that the invention may also provide a transgenic non-human animal comprising a transgene for a species-specific pathogen where the pathogen is restricted in its host range to any one or more of a number of species, including but not limited to, dogs, cats, horses, cattle, sheep or goats. Further, where the pathogen is "human-specific", the limited host range includes (or may be limited exclusively to) humans but excludes the selected laboratory animal. Where the pathogen is "species-specific", the limited host-range includes (or may be limited exclusively to) a particular species but excludes the selected laboratory animal.

In a preferred embodiment of the invention, the pathogen is a virus, and may be any RNA virus or DNA virus. The invention provides that the transgene comprising the virus may be a full length infectious provirus, a viral construct, or mutated with one or more mutations, including point, deletion, insertion, or rearrangement mutations that may or may not render the expressed virus non-infectious. Further, transcription of the viral transgene may be under the control of a promoter or enhancer, which may include heterologous promoters/enhancers affecting expression of the viral transgene. The invention provides that the receptor is any receptor that restricts infection of the selected virus to its host species or range, and may comprise any number of co-receptors acting together to mediate attachment and entry of the virus into the cells of the host species. The transgene or transgenes for the receptor or co-receptors may have one or more mutations, including point, deletion, insertion or rearrangement mutations that may result in altered function or may render the expressed receptor or receptors non-functional or unable to mediate entry of the selected virus into the cell.

In one embodiment of the invention, the human-specific pathogen is HIV, more preferably, is HIV-1, and most preferably is either a monocyte tropic isolate of HIV-1 or a T-cell tropic isolate of HIV-1. The receptors restricting infection of the virus into human cells comprise one or more of CD4, CXCR4 and CCR5 or other chermokine receptors capable of functioning as an HIV coreceptor, and are preferably CD4 and CXCR4 where the human-specific pathogen is HIV-1 from a T-cell tropic isolate of HIV-1, and CD4 and CCR5 where the human-specific pathogen is HIV-1 from a monocyte-tropic isolate of HIV-1.

The invention also provides a method for creating a transgenic non-human animal, comprising the steps of (a) isolating a fertilized oocyte from a female non-human donor animal; (b) transferring a transgene for a species-specific pathogen into the fertilized oocyte; (c) transferring the fertilized oocyte containing the transgene for a species-specific pathogen into the uterus of a female non-human surrogate animal; (d) maintaining said female non-human surrogate animal such that said female non-human surrogate animal gives birth to a transgenic non-human animal derived from the fertilized oocyte wherein said transgenic non-human animal comprises the transgene for the species-specific pathogen; (e) isolating a fertilized oocyte from a second female non-human donor animal; (f) transferring at least one transgene for a receptor restricting infection of the pathogen to the host species into the fertilized oocyte; (g) transferring the fertilized oocyte containing at least one transgene for a receptor restricting infection of the pathogen to the host species into the uterus of a second female non-human surrogate animal; (h) maintaining said second female non-human surrogate animal such that said second female non-human surrogate animal gives birth to a transgenic non-human animal derived from the fertilized oocyte wherein said transgenic non-human animal comprises at least one transgene for a receptor restricting infection of the pathogen to the host species; and (i) crossing the transgenic non-human animal comprising the transgene for the species-specific pathogen with the transgenic non-human animal comprising at least one transgene for a receptor restricting infection of the pathogen to the host species, such that the cross produces a transgenic non-human animal comprising a transgene for the species-specific pathogen and at least one transgene for a receptor restricting infection of the pathogen to the host species.

In a preferred embodiment of the invention, the host species is human (i.e., the host range includes humans or is limited exclusively to humans). Additionally, where the host species is human, the human-specific pathogen is preferably a virus, more preferably is HIV, and most preferably, HIV-1, although the invention contemplates the use of any strain of HIV in conjunction with the appropriate receptor or receptors. Alternate embodiments of the invention provide for virus obtained from T-cell tropic or, more preferably, monocyte-tropic isolates of HIV-1. The receptors used in the method of the present invention comprise one or more of CD4, CXCR4 and CCR5 (or other chemokine receptors capable of functioning as an HIV-1 co-receptor), and are preferably CD4 and CXCR4 where the human-specific pathogen is HIV-1 from a T-cell tropic isolate of HIV-1 and CD4 and CCR5 where the human-specific pathogen is HIV-1 from a monocyte-tropic isolate of HIV-1. The invention also provides for alternate methods of creating non-human transgenic animals which are well known in the art, including the introduction of the appropriate transgenes via embryonic stem cells.

Finally, the invention provides a method for screening an agent for the ability to inhibit infection by a species-specific virus, comprising administering the agent to be screened to a non-human transgenic animal comprising a transgene for a species-specific virus and transgene(s) for at least one receptor restricting infection of the species-specific virus to the host species, assaying viral replication by preferably measuring plasma HIV RNA levels of the non-human transgenic animal before and after administration of the agent being screened, and analyzing the effect of the administered agent on the viral levels of the non-human transgenic animal. In a preferred embodiment of the invention, the host species includes a human. In addition, the human-specific virus is preferably HIV, more preferably is HIV-1 and most preferably, is HIV-1 from a monocyte-tropic isolate or a T-cell tropic isolate of HIV. Where the HIV-1 is from a monocyte-tropic isolate of HIV-1, the receptor(s) are preferably one or more of CD4 and CCR5. Where the HIV-1 is from a T-cell tropic isolate of HIV-1, the receptor(s) are preferably one or more of CD4 and CXCR4. The selected agent may be a peptide, protein, nucleic acid, ribonucleic acid, antisense RNA, antibody, drug or compound.

The present invention is further described in the following Experimental Details Section which is set forth to aid in the understanding of the invention, and should not be construed to limit in any way the invention as defined in the claims which follow thereafter.

Experimental Details

A) huCD4/CCR5 Mice

Methods (i) Construction of CD4 and CCR5 Transgenes: A 3.2-kb NotI/BamHI fragment containing the proximal promoter for lymphocyte-specific protein tyrosine kinase p56lck (obtained from R. Perlmutter, University of Washington, Seattle) was blunted at the 5' NotI overhang and subcloned into pBluescript KS(−) at a blunted Kpn1 and a BamHI restriction site. The resulting plasmid, pLCK-A+, also contains 847 bp of simian virus 40 poly(A) tail coding sequence, which was inserted into the multicloning site at BamHI and Spel. A 1.1-kb DNA fragment containing the CCR5 gene with a 5' BamHI site and 3' XHOI site was generated by PCR amplification of human genomic DNA. The reaction was run for 30 cycles at 90° C. for 30 sec, 60° C. for 30 sec, and 68° C. for 2 min by using primers 5'-GTCTGAGTCTGA-GTCGGATCCAACAAGATGGATTATCAA (SEQ ID NO:1) and 3'-GTCTGAGTCTGAGTCCTCGAGTCCG TGTCACAAGCCCAC (SEQ ID NO:2) that have BamHI and XHOI sites and overlap the ATG and Stop codons, respectively. The amplified 1.1-kb CCR5 gene was digested with BamHI and XHOI and subcloned into the pLCK-A+ vector at the BamHI and SalI site. The resulting plasmid, pLCK-CCR5-A+, was digested with SfiI and NotI and purified for microinjection into mouse embryos. The plasmid pT4B (obtained from the National Institute of Allergy and Infectious Diseases AIDS Research and Reference Reagent Program, Bethesda, Md.) containing the human CD4 cDNA (Madden, et al., Cell 47:333–358, 1986) was digested with EcoRI and BamHI to obtain a 1.8-kb fragment containing the coding sequence. Blunt ends were generated at the 5' and 3' ends, and the CD4 cDNA fragment was inserted at the EcoRV site within pLCK-A+. Directionality of the CD4 insert was confirmed by restriction mapping. The construct was liberated by digestion of pLCK-CD4-A+ with SfiI and NotI and purified for microinjection into mouse embryos.

(ii) Detection of CD4 DNA and CCR5 DNA by PCR: DNA was extracted from transgenic mouse tails and purified by phenol extraction and alcohol precipitation. Human CD4 and CCR5 DNA were detected by PCR amplification (45 cycles at 94° C. for 30 sec, 65° C. for 30 sec, and 72° C. for 1 min) with taq polymerase (GIBCO/BRL) by using primers 5'-GTGGAGTTCAAAATAGACATCGTG-3' (SEQ ID NO:3) and 5'-CAGCACCCACACCGCCTTCT CCC GCTT-3' (SEQ ID NO:4), AND 5'-CACCTGCAGCTCTCATTTTCC-3' (SEQ ID NO:5) and 5'-TTGTAGGGAGCCCAGAAGAG-3' (SEQ ID NO:6) specific for the human CD4 and CCR5, respectively. No PCR products were detected after PCR amplification of control mouse DNA with these human CCR5 and CD4 primer pairs.

(iii) Flow Cytometric Analysis: Mononuclear cells harvested from the peripheral blood of the mice were stained with fluorescein isothiocyanate-conjugated mouse monoclonal antibody to human CD4 (Becton Dickinson) and/or phycoerythrin-conjugated rat monocular antibody to mouse CD4, CD8, or B220 (PharMingen), or with fluorescein isothiocyanate-conjugated mouse monoclonal antibody to human CCR5 (PharMingen) and phycoerythrin-conjugated mouse monocular antibody to CD4 (Becton Dickinson) as described (Kollman, et al., *J. Exp. Med.* 179; 513–522, 1994). Expression of the surface proteins was assessed by two color flow cytometric analysis by using a FACScan cell analyzer with LYSIS-II software (Becton Dickinson), and nonviable cells and unlysed red blood cells were gated out based on their forward- and side-scatter profiles.

(iv) Infection with HIV-1: Primary M-tropic HIV-1 strains HIV-1$_{59}$ (Kollman, et al., *J. Immunol.* 154:907–921, 1995) and 92RW009A, 92TH022E (WHO Network for Isolation and Characterization, *AIDS Res. Hum. Retroviruses* 10:1327–1343, 1994), HIV-1$_{JR-CSF}$, or HIV-1$_{JR-FL}$ (Koyanagi, et al., *Science* 236:819–826, 1987) obtained from the National Institute of Allergy and Infectious Diseases AIDS Research and Reference program were used. For in vitro infection, peripheral blood mononuclear cells (PBMCs) or splenocytes isolated by density centrifugation were cultured in microplates ($10^5$ cells per well) of the indicated isolate. The cultures were washed, and the p24 antigen content of the culture supernatant was measured at the indicated times by using the HIV-1 p24 core profile ELISA assay (DuPont/NEN). For in vitro infection, mice were inoculated with the indicated isolate by intrasplenic (300 TCID$_{50}$) or i.p. (8,000 TCID$_{50}$) injection. The mice were evaluated for evidence of HIV-1 infection at the indicated time by examining for the presence of HIV-1 gag DNA by DNA PCR, tat/rev RNA sequences by reverse transcription-PCR (RT-PCR), and infectious virus by coculture with activated human PBMCs as described (Kollman, et al., *J. Exp. Med.* 179:907–921, 1994). The positive control for detection of HIV DNA by PCR was HIV DNA (1,000 copies) obtained from 8E5 cells (from the NIH AIDS Research and Reagent Program) and for detection of HIV RNA by RT-PCR was RNA isolated from HIV-infected human T cells, and the negative controls were buffer and enzyme mixtures lacking DNA or cDNA as described (Kollman, et al., *J. Exp. Med.* 179:907–921, 1994).

Figure 1B:
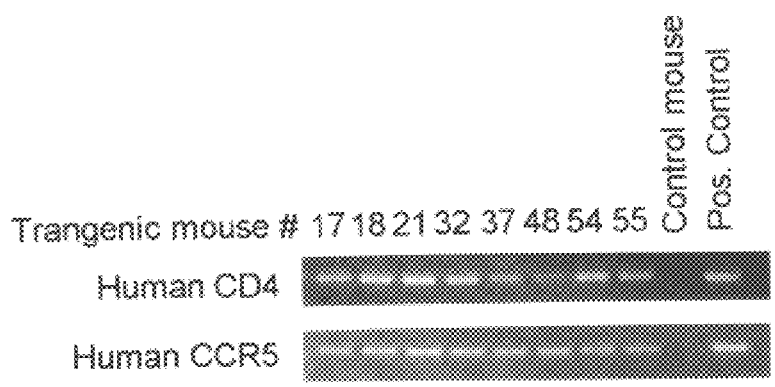
FIG. 1B depicts the detection of integrated human CD4 and CCR5 in the hu-CD4/CCR5 transgenic mice. DNA was extracted from the tails of the transgenic mice and integrated human CD4 and CCR5 were detected by PCR amplification with primer pairs specific for human CD4 and CCR5.
Figure 2A:
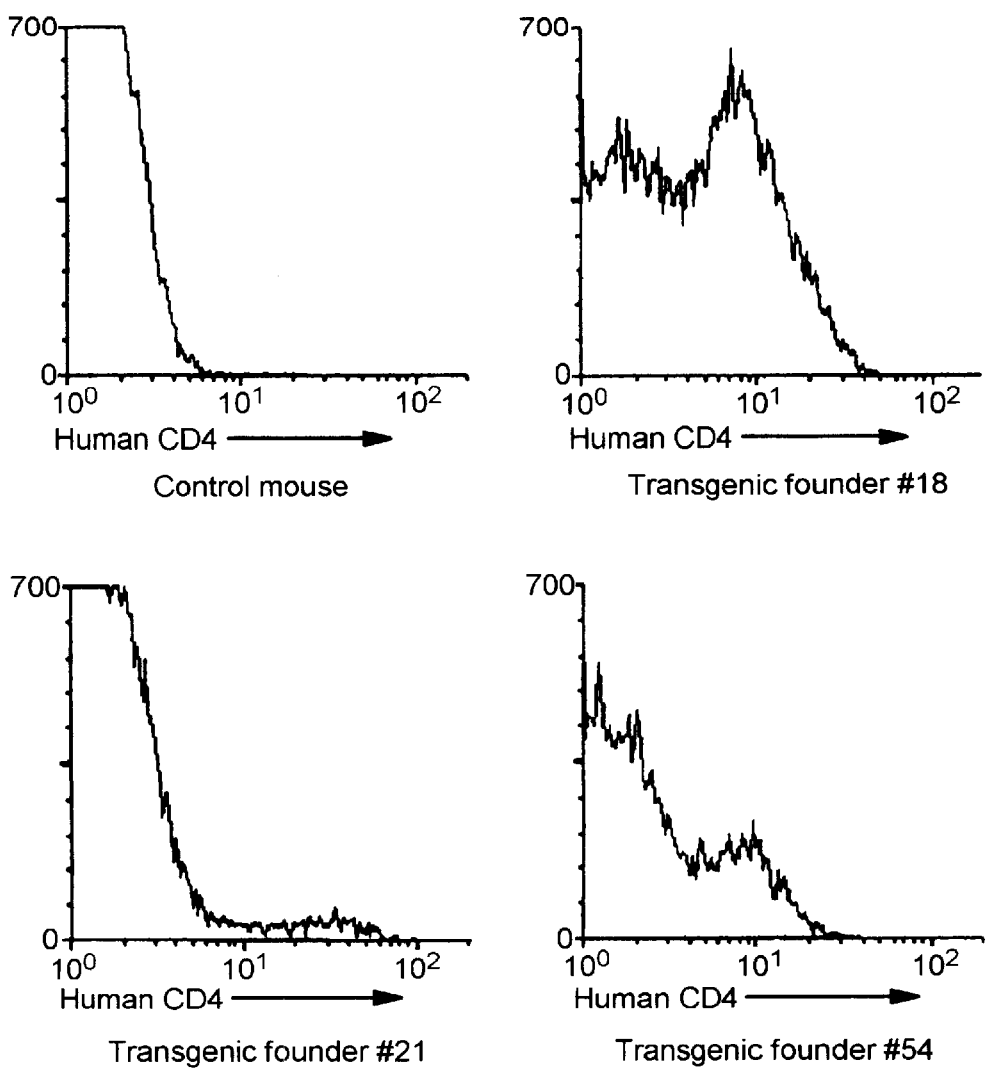
FIG. 2A depicts expression of human CD4 by PBMCs of transgenic mice. PBMCs were harvested from the transgenic founder mice, and surface expression of human CD4 was detected by flow cytometry by using a fluorescein isothiocyanate-conjugated mouse monoclonal antibody specifically directed against human CD4.
Figure 2B:
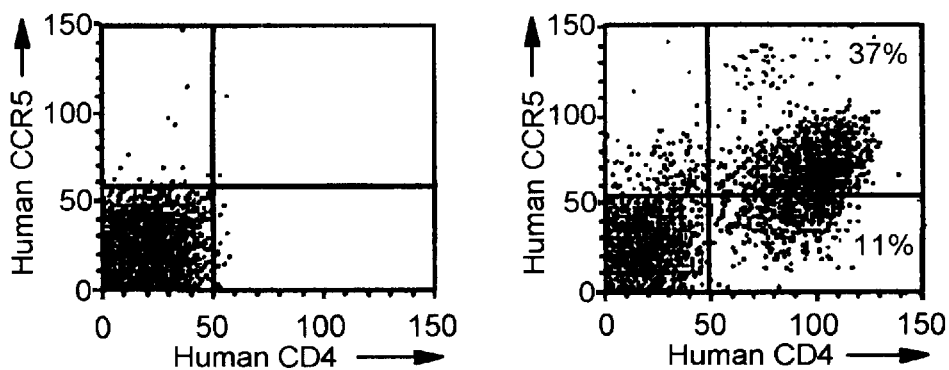
FIG. 2B depicts expression of human CCR5 by PBMCs of transgenic mice. PBMCs harvested from a transgenic mouse derived from transgenic founder mouse 18 and a control mouse were evaluated for surface expression of human CD4 and CCR5 by two-color flow cytometry by using mouse monoclonal antibodies specifically directed against human CD4 and CCR5. The percentage of positive cells in each quadrant is indicated.
Figure 3:
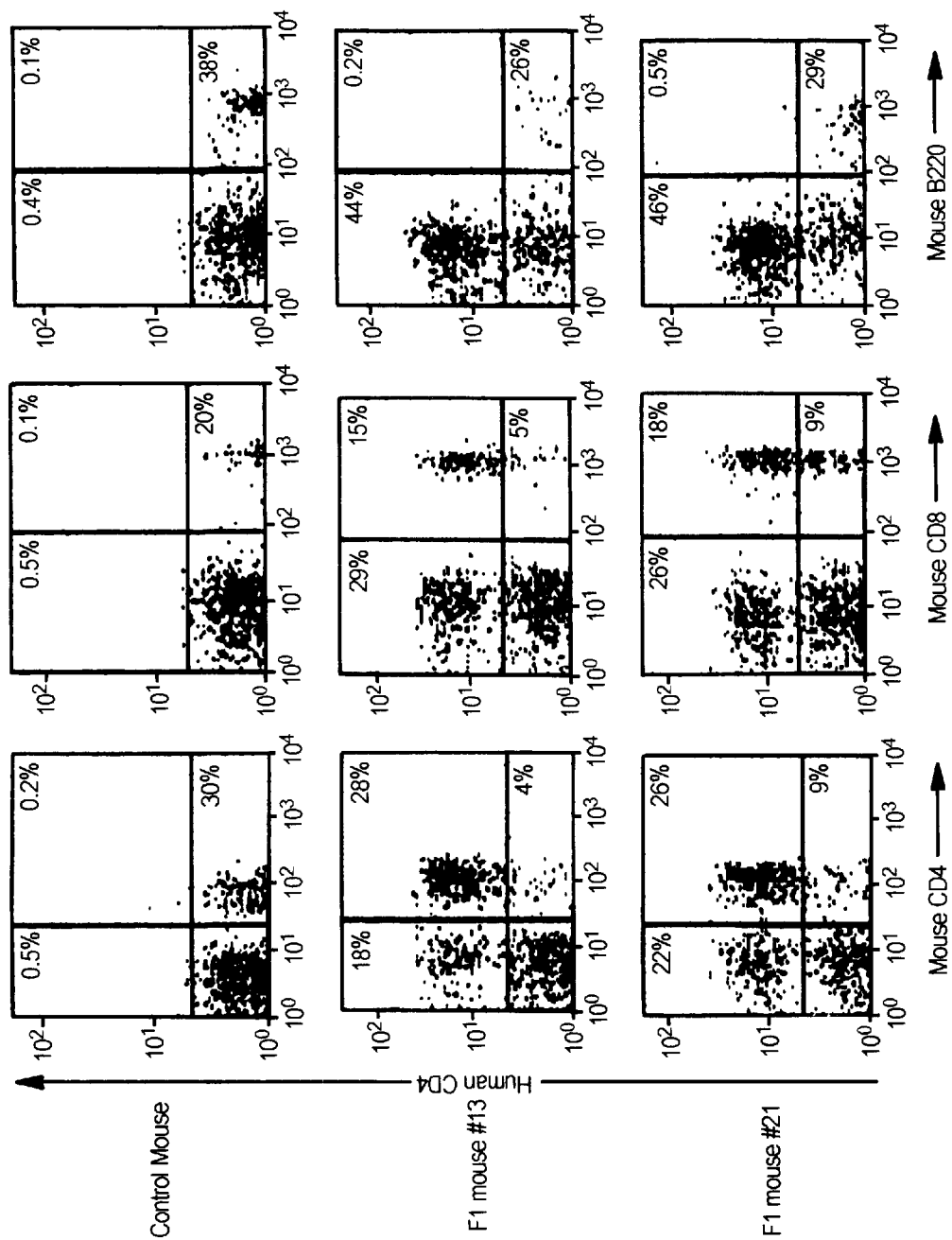
FIG. 3 illustrates selective expression of human CD4 by mouse T cells. PBMCs were isolated from a control mouse and two F1 progeny of founder mouse 18. Expression of human CD4 by the mouse CD4+ T-cells, CD8+ T cells and B cells were analyzed by two-color flow cytometry. The percentage of positive cells in each quadrant is indicated.

Results (i) Construction of Mice Transgenic for Human CD4 and CCR5: In vitro studies have demonstrated that mouse fibroblast cell lines such as 3T3 can become susceptible to HIV-1 entry after transient transfection with human CD4 and CCR5 expression vectors (Deng, et al., *Nature (London)*, 381: 661–667, 1996; Dragic, et al., *Nature (London)*, 381: 667–673, 1996). To further examine the role of CCR5 as a co-receptor for HIV-1, several independent mouse lines transgenic for both human CD4 and CCR5 were developed and it was determined whether lymphocytes obtained from these mice could become infected with HIV-1. Although M-tropic HIV-1 isolates can infect both monocytes and peripheral T cells, T cells are the critical target for HIV-1 infection as evidenced by their production of greater than 90% of the plasma virus present in infected individuals (Perelson, et al., *Science* 271:1582–1586, 1996; Chun, et al., Nature (London) 387:183–188, 1997). Therefore, the T cell-specific lck promoter (Wilden, et al, J. Exp. Med. 173:383–393, 1991) was used to construct vectors LCK-CD4-A+ and LCK-CCR5-A+ (FIG. 1A) targeting expression of human CD4 and CCR5 to T cells in the transgenic mice. Transgenic founders harboring both transgenes were generated by co-microinjection of these constructs into the pronuclei of F2 hybrid oocytes from FVBxC57/B6 parents as described (Hogan, et al., *Manipulating the Mouse Embryo: A Laboratory Manual*, 1986). Of 54 offspring, PCR analysis of tail DNA identified 10 transgenic founder mice that had integrated both the LCK-CD4-A+ and LCK-CCR5-A+ constructs (FIG. 1B). Flow cytometric analysis using a monoclonal antibody specific for human CD4 demonstrated that three of these transgenic founder mice expressed varying levels of human CD4 on the cell surface of their PBMCs (FIG. 2A). In addition, human CCR5 mRNA was detected in PBMCs isolated from these three transgenic founder mice by RT-PCR. Expression of both human CD4 and CCR5 expression on the surface of PBMCs isolated from progeny of transgene founder mouse 18 was demonstrated by two-color flow cytometric analysis (FIG. 2B). Human CD4 and CCR5 expression were detected in 5 of 10 progeny of transgene founder mouse 18, suggesting that the integrated genes in this transgenic line were in strong linkage disequilibrium and most likely integrated in tandem. To determine whether human CD4 was expressed on T cells, two-color flow cytometry analysis was performed on the mouse PBMCs to evaluate human CD4 expression by the CD4+ T cells, CD8+ T cells, and B cells in the peripheral blood of two F1 mice derived from transgene founder mouse 18. Although human CD4 was expressed on the majority of mouse CD4+ and CD8+ T cells, it was not detected on the mouse B cells (FIG. 3), indicating that the lck promoter was directing expression of the transgene to the mouse T cells as expected. (See Browning, et al., *Immunology* 94:14637–14641, 1997, the complete contents of which are expressly incorporated herein).

Figure 4:
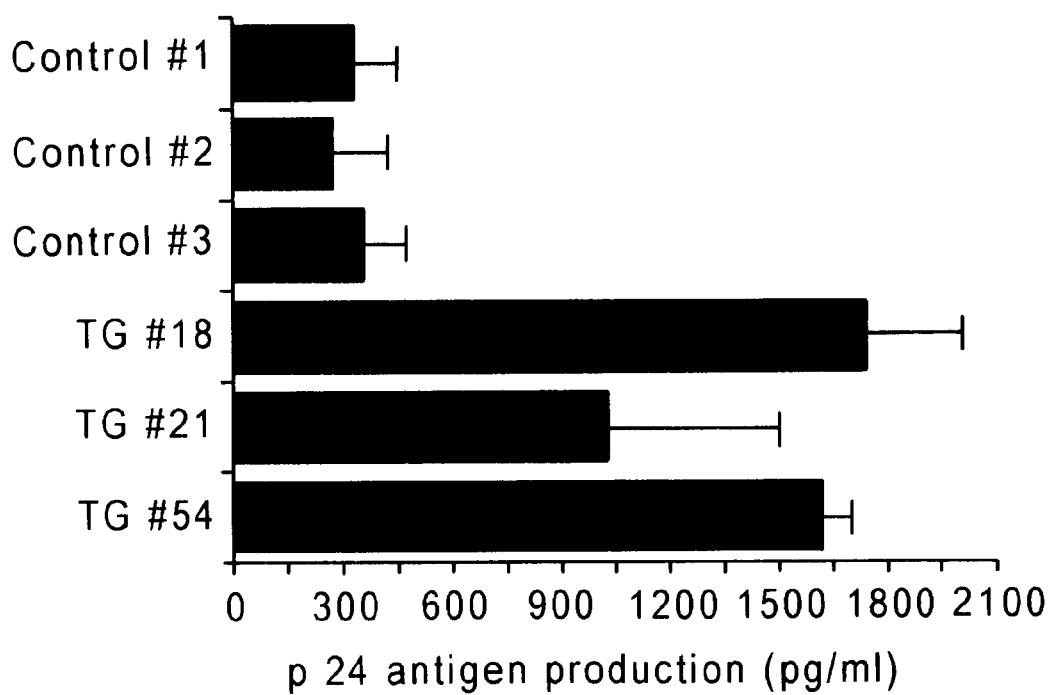
FIG. 4 sets. forth a graph showing HIV infection of the PBMCs of the hu-CD4/CCR5 founder mice. Peripheral blood mononuclear cells from three founder mice and three control mice were infected with HIV-$1_{59}$ at a multiplicity of infection of 0.025 (4,394 pg of p24). Three days after infection the cells were extensively washed, and six days later the level of p24 antigen in the culture supernatant was determined. The data shown are the mean ±SEM of two separate experiments.

(ii) In Vitro Infection of Leukocytes from Human CD4/CCR5 Transgenic Mice: To determine the susceptibility of leukocytes from these transgenic mice to infection by HIV-1, PBMCs isolated from founder transgenic mice and control mice were incubated with a primary patient M-tropic isolate of HIV-1, HIV-$1_{59}$. Three days later, the cultures were washed, and 6 days later the culture supernatants were evaluated for the presence of HIV p24 antigen. Productive HIV-1 infection indicated by the presence of this antigen in the culture supernatant was detected in cultures of PBMCs from the transgenic mice and not in cultures of PBMCs from the control mice (FIG. 4). The extent of HIV-1 infection in the PBMCs from the transgenic mice correlated with cellular expression of human CD4. Cultures containing cells from transgenic mouse 18, which had the highest level of human CD4 expression, produced the most p24 antigen, and cultures containing cells from transgenic mouse 21, which had the lowest level of human CD4 expression, produced the least p24 antigen.

To further evaluate the in vitro sensitivity of leukocytes from the human CD4/CCR5 transgenic mice to infection with HIV-1, splenocytes from transgenic mouse 18 were harvested and infected with several isolates of HIV-1. After 6 days of culture, the cells were washed, and then the p24 antigen concentration in the culture supernatant was measured on day 6, day 8, and day 11 of culture. After 11 days of culture, the splenocytes were further evaluated for integrated HIV-1 by gag-specific DNA PCR and for active viral replication by RT-PCR detection of spliced tat/rev RNA sequences. Infection by HIV-1 isolates HIV-$1_{JR\text{-}CFS}$, HIV-$1_{JR\text{-}FL}$, and HIV-$1_{59}$ was indicated by the production of increasing amounts of p24 antigen (FIG. 5A) and the detection of HIV-1 gag DNA (FIG. 5B) and tat/rev RNA (FIG. 5C) sequences in the transgenic mouse splenocytes. In comparison, 1–2 weeks after infection of human PBMCs with the same inoculum of HIV-$1_{JR\text{-}CFS}$, HIV-$1_{JR\text{-}FL}$, HIV-$1_{59}$, 92rw009a, and 92TH022E isolates, p24 antigen production of 34,655, 29,935, 43,945, 37,045, and 33,848 pg/ml, respectively, was obtained.

(iii) In Vivo Infection of Human CD4/CCR5 Transgenic Mice: The susceptibility of the human CD4/CCR5 transgenic mice to in vivo HIV-1 infection was evaluated by inoculating them with different HIV-1 strains either by intrasplenic injection or by i.p. injection. As shown in the Table 1 below, although HIV-1 gag DNA sequences were present in monocular cells isolated from the spleen and lymph nodes of the human CD4/CCR5 transgenic mice 4 weeks after inoculation, HIV-1 tat/rev RNA sequences were not detectable by RT-PCR and HIV-1 could not be isolated by coculture (data not shown). Thus, although expression of human CD4 and CCR5 in the transgenic mice overcame the block that prevented entry of HIV-1 into mouse cells, sustained in vivo replication of HIV-1 still did not occur.

TABLE 1

In vitro infection of human CD4/CCR5 transgenic mice

| Mouse | Isolate | Time (wks) | Spleen | | | Lymph Node | | |
|---|---|---|---|---|---|---|---|---|
| | | | gag | tat/rev | Coculture | gag | tat/rev | Coculture |
| Control | | | | | | | | |
| #1 | HIV-$1_{59}$ | 2 | – | – | – | – | – | – |
| #2 | HIV-$1_{59}$ | 4 | – | – | – | – | – | – |
| #3 | HIV-$1_{59}$ | 4 | – | – | – | – | – | – |
| #4 | HIV-$1_{1779}$ | 4 | – | – | – | – | – | – |
| TG | | | | | | | | |
| #1 | HIV-$1_{59}$ | 2 | – | – | – | – | – | – |
| #2 | HIV-$1_{59}$ | 2 | – | – | – | – | – | – |
| #3 | HIV-$1_{59}$ | 4 | + | – | – | ND | – | – |
| #4 | HIV-$1_{1779}$ | 4 | – | – | – | + | – | – |
| #5 | HIV-$1_{59}$ | 4 | + | – | – | – | – | – |

TABLE 1-continued

In vitro infection of human CD4/CCR5 transgenic mice

| Mouse | Isolate | Time (wks) | Spleen | | | Lymph Node | | |
|---|---|---|---|---|---|---|---|---|
| | | | gag | tat/rev | Coculture | gag | tat/rev | Coculture |
| #6 | HIV-1$_{JR-CSF}$ | 4 | + | − | − | + | − | − |
| #7 | HIV-1$_{JRFL}$ | 4 | + | − | − | − | − | − |

Mice were infected by intrasplenic inoculation of 300 TCID$_{50}$ (control #1, #2, #3, and TG #1, #2, and #3) or i.p. injection of 8,000 TCID$_{50}$ (control #4 and TG #4, #5, and #6) of the indicated isolate. TG #4, #5, and #6 were inoculated weekly four times. The mice were sacrificed and the splenocytes and lymph node cells were evaluated for HIV gag DNA and tat/rev RNA by PCR and for the presence of infectious virus by coculture. ND, not done.

Discussion

The experimental methods and results above provide verification that in vivo expression of human CD4 and CCR5 in primary mouse lymphocytes permits these cells to be infected with primary HIV-1 isolates. Low levels of productive in vitro infection of the transgenic mouse splenocytes was indicated by the rise in p24 antigen levels produced during the course of culture after infection with certain M-tropic isolates, HIV-1$_{59}$, HIV$_{JR-CSF}$, and HIV$_{JR-FL}$, but not with others such as 92RW009A and 92TH022E. Cellular infection was indicated further by the infection of HIV-1 gag DNA and spliced tat/rev RNA in the cells. The observation that the transgenic mouse splenocytes were infected by some M-tropic isolates and not by others suggested that different HIV-1 isolates may have varying capacity to productively infect mouse cells.

The major barrier preventing HIV-1 infection of mouse cells, a block in cellular penetration because of structural differences between human and mouse CD4 and CCR5, was overcome by the expression of human CD4 and CCR5 by T cells in these transgenic mice. Although leukocytes from the human CD4/CCR5 transgenic mice were infectible with HIV-1 in vitro, the degree of p24 antigen production was 1–2 logs less than that observed after infection of human leukocytes, and infectious virus was not isolated from the culture supernatant by secondary coculture with human PBMCs (data not shown). The decreased replication of HIV-1 in mouse cells has been attributed to the reduced function of certain HIV-1 regulatory genes in mouse cells (Chesebro, et al., *J. Virol.* 64: 4553–4557, 1990). The activity of HIV-1 tat, the major positive regulator of HIV-1 gene expression, is markedly decreased in mouse cell lines (Winslow & Trono, *J. Virol.* 67:2349–2354; 1993). The resistance of mouse cells to tat-mediated trans-activation is a result of the absence of a species-specific cofactor encoded by human chromosome 12 that is required for the binding of Tat to its cis-responsive binding element, TAR (Newstein, et al., *J. Virol.* 64: 4565–4567, 1990). The function of another HIV-1 regulatory gene product, Rev, which facilitates transport of incompletely spliced HIV-1 mRNAs from the nucleus into the cytoplasm, is also markedly diminished in mouse fibroblast cell lines (Winslow & Trono, *J. Virol.* 67: 2349–2354, 1993; Trono & Baltimore, *EMBO J.* 9:4155–4160, 1990) However, although the activity of Tat and Rev may be restricted in some mouse tissues such as fibroblasts, they may be functional in other mouse tissues such as lymphoid cells. For example, substantial Tat-mediated trans-activation was detected in a mouse macrophage line, RAW264, that was mediated by interaction between Tat and TAR (Murphey, et al., *J. Virol.* 67:6956–6964, 1993).

Furthermore, although Rev function was severely blocked in some mouse cell lines, functional Rev activity was observed in a murine T cell hybridoma (Newstein, et al., *J. Virol.* 64: 4565–4567, 1990). Thus, sufficient activity of these regulatory genes may occur in the T cells from the human CD4/CCR5 transgenic mice, permitting them to be infected with HIV-1 albeit at a much lower level than human T cells. Nevertheless, the results indicated that these levels were insufficient to permit sustained productive in vivo infection in mice transgenic for human CD4 and CCR5. It is also possible that the absence of in vivo HIV-1 replication in these mice was a result of the defective function of other HIV-1 regulatory genes in mouse cells, such as vif, which is responsible for the production of infectious virions (Von Schwedler, et al., *J. Virol.* 67:4945–4955, 1993) and the lack of other factors required for virion assembly and budding.

Taken together, these results indicated that although expression of human CD4 and a chemokine receptor such as CCR5 may be sufficient to permit entry of HIV-1 into mouse cells, the combined effect of impairment in other stages of HIV-1 replication in mouse cells may prevent the development of sustained in vivo infection in these human CD4/CCR5 transgenic mice. Therefore, the presence of additional blocks that prevent efficient HIV-1 replication in mouse cells complicates the use of transgenic mice to investigate the immunopathology of HIV-1 infection. It is possible that modification of HIV-1 proviruses so that they contain alternate regulatory genes that are active in mouse cells would permit productive infection to occur in these mice. For example, when the murine leukemia virus (MLV) core enhancer was inserted into the HIV-1 LTR, increased transcriptional activity of the HIV-1 LTR was observed in mouse cells, and mice transgenic for an HIV-1 LTR was observed in mouse cells, and mice transgenic for an HIV-1 provirus containing this MLV/HIV chimeric long terminal repeat produced infectious virus particles (Dickie, et al., *AIDS Res. Hum. Retroviruses* 12:1103–1117, 1996). If productive infection would occur in these human CD4/CCR5 transgenic mice after infection with modified HIV-1 proviruses, then they could be used to examine whether a vaccine-stimulated immune response could prevent infection. Thus, the human CD4/CCR5 transgenic mice described in this report represent a productive first step in the development of a new in vivo system to evaluate the effectiveness of candidate HIV-1 vaccines and to study the pathobiology of HIV-1 infection.

B) JR-CSF Mice

Methods (i) Construction of transgenes: An infectious molecular clone of HIV-1$_{JR-CSF}$, PYK-JR-CSF, obtained from the NIH AIDS Research and Reference Reagent Program was used to construct the transgene. PYK-JRCSF, cloned from infected peripheral blood lymphocytes 11 days after the initiation of culture, contains the full length genomic sequence of HIV-1$_{JR-CSF}$ well as 0.5 kb and 2.2 kb of 3' and 5' flanking sequences, respectively, and produces infectious virions after transfection into cells (Koyanagi Y., et al., *Science* 236:819–822, 1987; Cann A. J., *J. Virol.* 64:4735–4742, 1990). The PYK-JRCSF plasmid was linearized with EcoR1, and then microinjected into the pronuclei of fertilized embryos derived from FVB/N×FVB/N mouse crosses as described (Browning, J., et al., *Nature* 382:722–725, 1997). Because the transgene was controlled by the HIV-1 LTR, HIV transcription should occur in tissues in which HIV LTR is active. JR-CSF transgenic mice were identified by analysis of genomic DNA extracted from tails for integrated HIV with PCR using primer pairs specific for the amplification of HIV-1 gag DNA as described (Kollmann, T. R., et al., *J. Exp. Med.* 179:513–522, 1994).

(ii) Flow cytometric analysis: Mononuclear cells harvested from the peripheral blood of the JR-CSF TG mice were stained with fluorescein isothiocyanate-conjugated mouse monoclonal antibody to HIV gp120 (American Research Products, Belmont, Mass.) and phycoerythrin conjugated rat monoclonal antibody to mouse CD8 or B220 and Peridinian chlorophyll protein (PerCP)-conjugated CD4 (PharMingen, San Francisco, Calif.) as described (Kollmann, T. R., et al., *J. Exp. Med.* 177:821–834, 1993). Expression of the surface proteins was assessed by three-color flow cytometric analysis using a FACScan cell analyzer with LYSIS-III software (Becton Dickinson) and non-viable cells and unlysed red blood cells were gated out based on their forward and side scatter profiles.

(iii) Detection of HIV-1 production: PBMCs, splenocytes and thymocytes isolated from the JR-CSF TG mice by density centrifugation were cultured in microplates ($10^5$ cells/well) with PHA-activated donor PBMCs ($3\times10^5$ cells/well) in RPMI media containing 7% FCS/5% IL-2/2-ME (50 $\mu$M) as described (Kollmann, T. R., et al., *J. Exp. Med.* 179:513–522, 1994). After 4 days of culture, fresh activated donor PBMCs were added to the cultures and supernatant was harvested at the indicated times for measurement of p24 antigen content and secondary coculture. The p24 antigen content of the culture supernatant was measured at the indicated times using the HIV-1 p24 core profile ELISA assay (Dupont-NEN). For secondary coculture, 100 $\mu$l of the culture supernatant was added to new cultures containing PHA-activated donor PBMCs ($3\times10^5$ cells/well) in RPMI media containing 7% FCS/5% IL-2/2-ME (50 $\mu$M) in a total volume of 1 ml and after 7 days, the p24 antigen content of the culture supernatant was measured.

(iv) Quantitation of plasma HIV RNA levels: HIV RNA in the mouse plasma was quantitated by using the Roche AMPLICOR HIV-1 MONITOR™ kits (Roche Diagnostic Systems, Branchburg, N.J.) which can measure virion associated HIV-1 RNA in plasma at concentrations as low as 400 RNA copies/ml as described (Pettoello-Mantovani, M., et al., *J. Infect. Dis.* 1 77:337–346, 1998). After plasma was isolated from the peripheral blood of the JR-CSF TG mice, an internal HIV quantitation standard (QS), a synthetic RNA molecule with primer binding sites identical to the HIV target and an internal probe sequence specific to the QS RNA molecule, was added to 200 $\mu$l of each plasma sample. RNA was then extracted from the plasma samples with a Lysis Reagent containing guanidine thiocyanate, precipitated with isopropanol, resuspended in reaction buffer and a 142 base pair sequence in the HIV gag gene was amplified by reverse transcription and PCR using rtth pol and biotinylated primers SK431 and SK462. In order to prevent PCR product contamination, dUTP was incorporated during the PCR reaction and then all of the samples were treated with AmpErase prior to PCR to eliminate carryover of any dUTP-containing PCR product. The biotinylated HIV and QS amplicons were quantitated by detection in separate wells of a microwell plate coated with HIV-specific and QS-specific oligonucleotide probes, respectively, using avidin-horseradish peroxidase conjugate and a calorimetric reaction for horseradish peroxidase. The HIV and QS amplicons were measured in a dynamic range from 400 to 750,000 copies/ml by performing 5-fold serial dilutions of the amplicons in the HIV-specific and QS-specific wells of the microplate (rows A to F and G to H, respectively). The HIV RNA copy number was then calculated from the known input copy number of the QS RNA, the optical densities at 450 nm of the HIV-well and the QS-well that fell within a defined range, and the dilution factors associated with the selected wells.

(v) In vivo stimulation of T cells with bacterial superantigen: Baseline plasma HIV RNA levels in JR-CSF transgenic mice were determined as described above. A pair of the transgenic mice were then injected intraperitoneally with either 50 $\mu$g of staphylococcal enterotoxin B (SEB) or with an equivalent volume of PBS. At 24 hours and 72 hours after the indicated treatment, the mice were bled and the plasma HIV RNA levels were measured.

(vi) In situ hybridization: Detection of HIV RNA by in situ hybridization was performed as described (Gibbons, et al., *AIDS Res. Hum. Retro.* 13:1453–1460 (1997). Paraffin-embedded tissue was sectioned (6–8 $\mu$M) onto charged slides (Superfrost/Plus, Fisher Scientific, Pittsburgh, Pa.), deparaffinized with 3 washes of 100% xylene, rehydrated, washed with 0.2 N HCl, rinsed in PBS, treated with proteinase K (200 $\mu$g/ml) for 30 min at 37° C. and postfixed with 4% paraformaidehyde for 10 min. The slides were prehybridized overnight at 37° C. in a humidified chamber with hybridization buffer [50% formamide, 2×SSC, 1×Denhardt, 10% Dextran, salmon sperm DNA (100 $\mu$g/ml) and yeast T-RNA (25 $\mu$g/ml)] and then probed with digoxigenin-labeled RNA probe (Boehringer Mannheim Biochemicals Genius 4 Labeling Kit) which spanned the gag regions mixed with hybridization buffer (1:150) at 37° C. overnight in a humidified chamber. After hybridization, the slides were washed sequentially with 2×SSC for 15 min at 23° C., with 2×SSC/50% formamide at 42° C. for 15 min, 2×SSC/1 mM EDTA/0.1% Triton X-100 at 60° C. for 15 min, and with 0.1×SSC/0.5 M EDTA at 60° C. for 15 min. The slides were next incubated in Genius I buffer (0.1M Tris-HCl/0.15M NaCl, pH 7.5) for 5 min, blocked with 5% FCS in Genius II buffer for 15 min at 23° C., incubated with alkaline phosphatase-conjugated anti-digoxigenin antibody (1:100 in Genius II buffer) for 30 min at 23° C., sequentially washed twice for 5 minutes each in Genius I buffer and then washed for 2 min in Genius III buffer [0.1M Tris-HCl (pH 9.5)/0.1M NaCl/0.05M $MgCl_2$. The slides were then incubated with substrate (4.5 $\mu$l NBT/3.5 $\mu$l BCIP/mi in Genius III buffer) overnight. After rinsing with $H_2O$, the slides were dehydrated, washed in xylene, and coverslipped with Permount (Fisher Scientific). Specificity of the reaction was confirmed by parallel processing of tissues probed with the sense probe and HIV uninfected tissues probed with the anti-sense probe.

Results (i) Construction of mice transgenic for HIV-1 JR-CSF: The JR-CSF TG mouse lines were generated using a plasmid, PYK-JRCSF, that contains a full length copy of proviral DNA cloned from the PBMCs of an HIV-infected individual soon after the initiation of coculture that after cellular transfection generates an infectious HIV-1 isolate, HIV-$1_{JR-CSF}$ (Koyanagi Y., et al., *Science* 236:819–822, 1987; Cann A. J., *J. Virol.* 64:4735–4742, 1990). Transgenic founders that harbored the HIV provirus were generated after microinjection of the construct into the pronuclei of F2 hybrid oocytes from FVB×C57/B6 parents as described (Browning, J., et al., *Nature* 382:722–725, 1997). Of 40 offspring produced, PCR analysis of tail DNA identified 7 transgenic founder mice that had integrated HIV-1 gag sequences. Founder mice #16 and #24 were bred and HIV DNA was detected in 13 of 27 F1 progeny of transgene founder mouse #16 and 9 of 19 F1 progeny of transgene founder mouse #24. Transmission of the transgene in these two lines followed a Mendelian pattern of distribution that indicated that there was no lethality associated with expression of the transgene.

(ii) Mice transgenic for HIV-1$_{JR\text{-}CSF}$ produce infectious virus: To determine whether cells from these transgenic lines produced infectious virus, the founder mice were bled, and PBMCs were isolated and cocultured with activated human PBMCs. After 7 days of culture, p24 antigen was detectable in the coculture of PBMCs from 3 founder mice ranging from the low level in cocultured PBMCs from founder #16 to higher levels in cocultured from PBMCs from founder #15 and founder #24 (Table 2).

TABLE 2

Coculture of PBMCs from transgenic founders with activated human PBMCs.

| | IL-2-stimulated mouse PBMCs | IL-2/Con A-stimulated mouse PBMCs |
|---|---|---|
| Control Mouse | 0.1 | 0.1 |
| TG mouse # | | |
| 2 | 0.1 | 0.1 |
| 5 | 0.1 | 0.1 |
| 15 | >100 | >100 |
| 16 | 58 | 58 |
| 23 | 0.1 | 0.1 |
| 24 | >100 | >100 |
| 25 | 0.1 | 0.1 |

Mouse PBMCs isolated from the indicated transgenic mouse was cocultured with activated human donor PBMCs. After 7 days of culture, the concentration of p24 antigen (pg/ml) in the culture supernatant was determined.

Figure 6A:
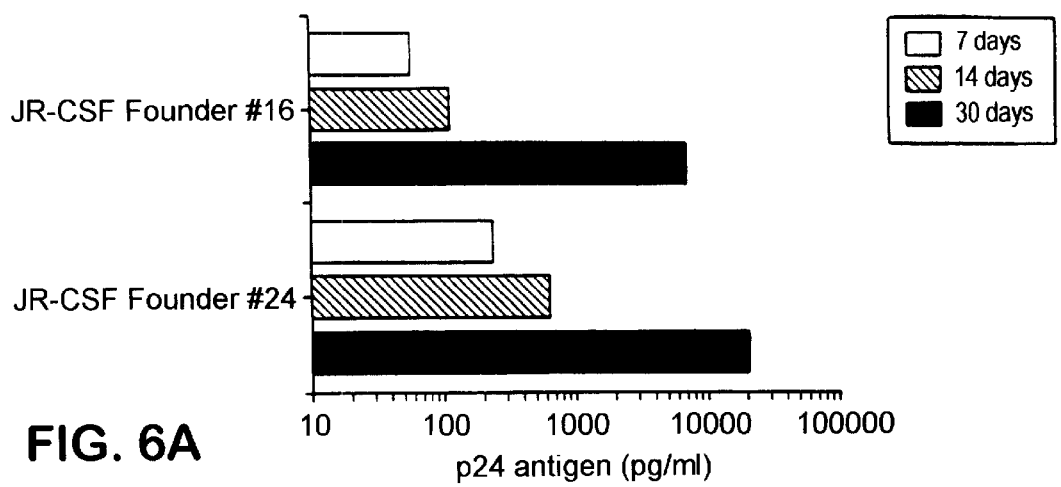
FIGS. 6(A–C) sets forth a graph showing production of HIV-1 by JR-CSF leukocytes. (A) PBMCs from founder mice #16 and #24 were isolated, cocultured with PHA-activated human PBMCs and the p24 antigen concentration of the supernatant was assayed at the indicated time points. (B) PBMCs from the progeny of founder mouse #24 were separated from PHA-activated human PBMCs by a. 3 μm filter and cocultured for one month. At the indicated time, an aliquot of the supernatant was obtained from the well containing the human PBMCs and assayed for p24 antigen concentration. (C) Splenocytes ($2\times10^6$ cells/mil) from the JR-CSF mice were either unstimulated or stimulated with αCD3-ε coupled to the culture dish for two days and then the p24 antigen concentration was determined.

To evaluate whether HIV production by PBMCs from the JR-CSF transgenic mice increased over time, the amount of p24 antigen produced by the cocultured PBMCs isolated from transgenic founder mice #16 and #24 was measured at different time points. After three days of culture, the cells were washed and then the p24 antigen concentration in the culture supernatant was measured on day 7, day 14 and day 30 of culture. The p24 antigen concentration of the supernatant increased during culture, with high levels of p24 antigen detectable 30 days after the initiation of coculture of PBMCs from all 3 founders, and the most rapid rise and highest level of p24 antigen production displayed by the PBMCs from founder #24 (FIG. 6A).

Figure 6B:
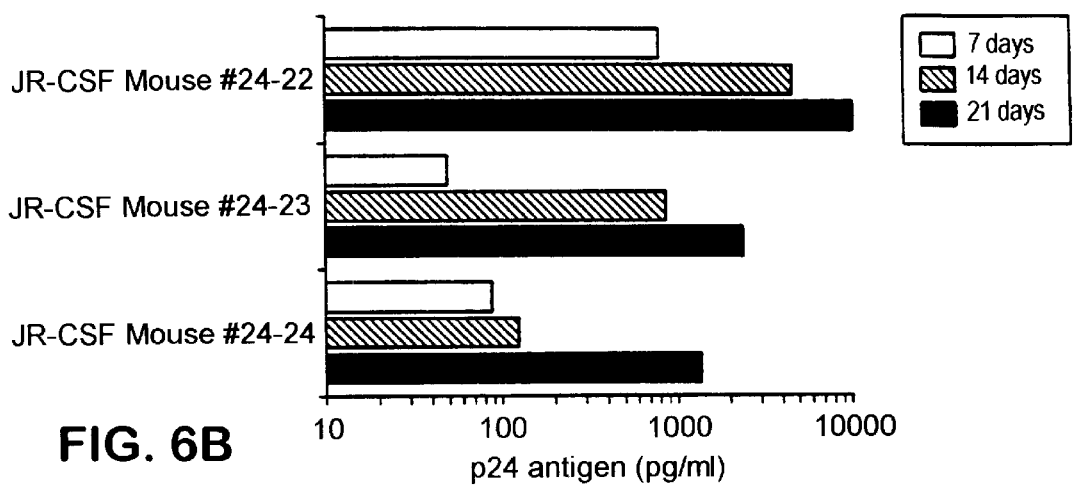

However, it was still possible that the transgenic mouse cells did not directly produce infectious virus but rather activated human donor PBMCs that fused with transgenic mouse cells were the source of virus. Therefore, cocultures were performed in transwell culture dishes in which the PBMCs isolated from 3 F1 mice derived from transgene founder mouse #24 were separated from the activated human donor PBMCs by a 3 μM-polyester membrane. As shown in FIG. 6B, high levels of p24 antigen were detected in the culture supernatant, indicating that the mouse PBMCs were producing infectious HIV-1 that crossed the transwell membrane and then infected the activated human PBMCS.

Figure 6C:
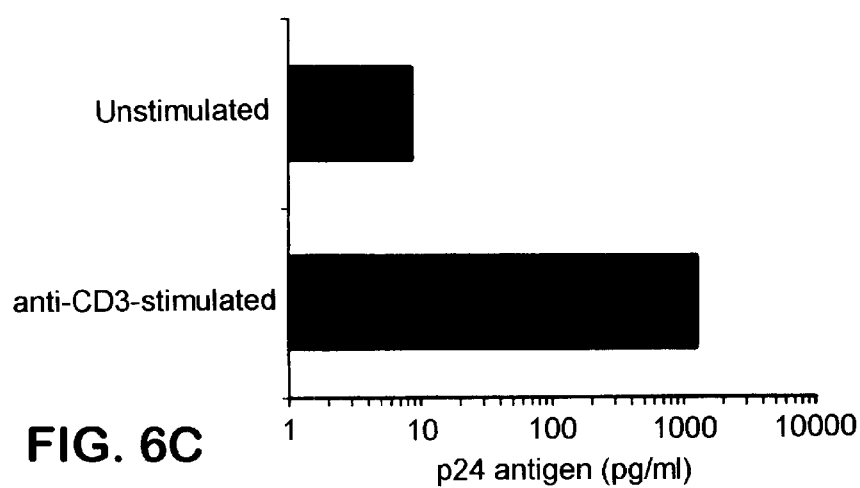

We further investigated the capacity of leukocytes from the JR-CSF mice to produce HIV-1 by measuring the concentration of p24 antigen produced by JR-CSF mouse splenocytes cultured in the absence of human cells. Because expression of the JR-CSF transgene is regulated by the HIV LTR in the construct, we also examined whether production of HIV-1 by JR-CSF mouse splenocytes would be increased by stimulation with anti-CD3. As shown in FIG. 6C, low levels of p24 antigen were detected in the supernatant of cultured JR-CSF:splenocytes that increased over 100-fold by stimulation of the splenocytes with anti-CD3. To confirm that infectious HIV-1 was produced by the JR-CSF mouse splenocytes, an aliquot of the culture supernatant (containing about 100 pg of p24 antigen) was placed in secondary coculture in triplicate with fresh activated human PBMCs. After 7 days, the culture supernatant was measured and contained 54,281±3,987 pg of p24 antigen. Thus, HIV-1 production by the JR-CSF mouse leukocytes was responsive to stimulation with anti-CD3 and the HIV-1 secreted into the supernatant by these stimulated cells was infectious.

Figure 7A:
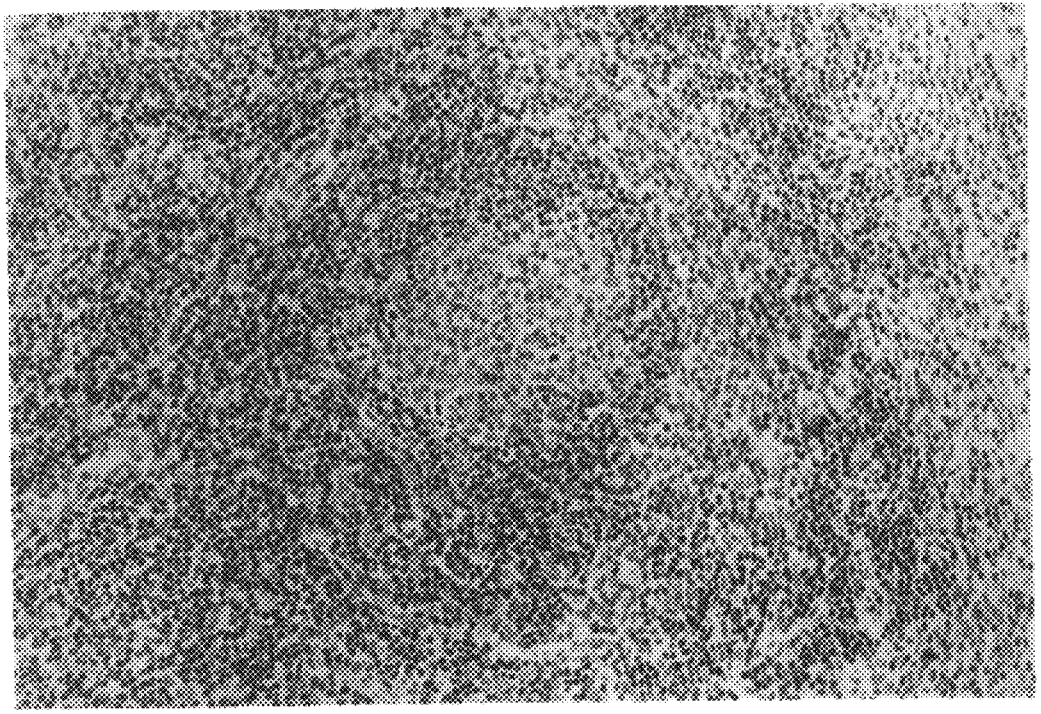
FIGS. 7(A–D) sets forth a histological appearance of lymphoid tissues from JR-CSF transgenic mice and wild-type mice. Photomicrographs of hematoxalin and eosin stained sections of the spleen from the JR-CSF transgenic mouse (A) and the wild-type mouse (B), and the thymus from the JR-CSF transgenic mouse (C) and the wild-type mouse (D). Photographs were taken 200× magnification and are representative of tissues from 3 JR-CSF transgenic mice and 3 wildtype mice.
Figure 7B:
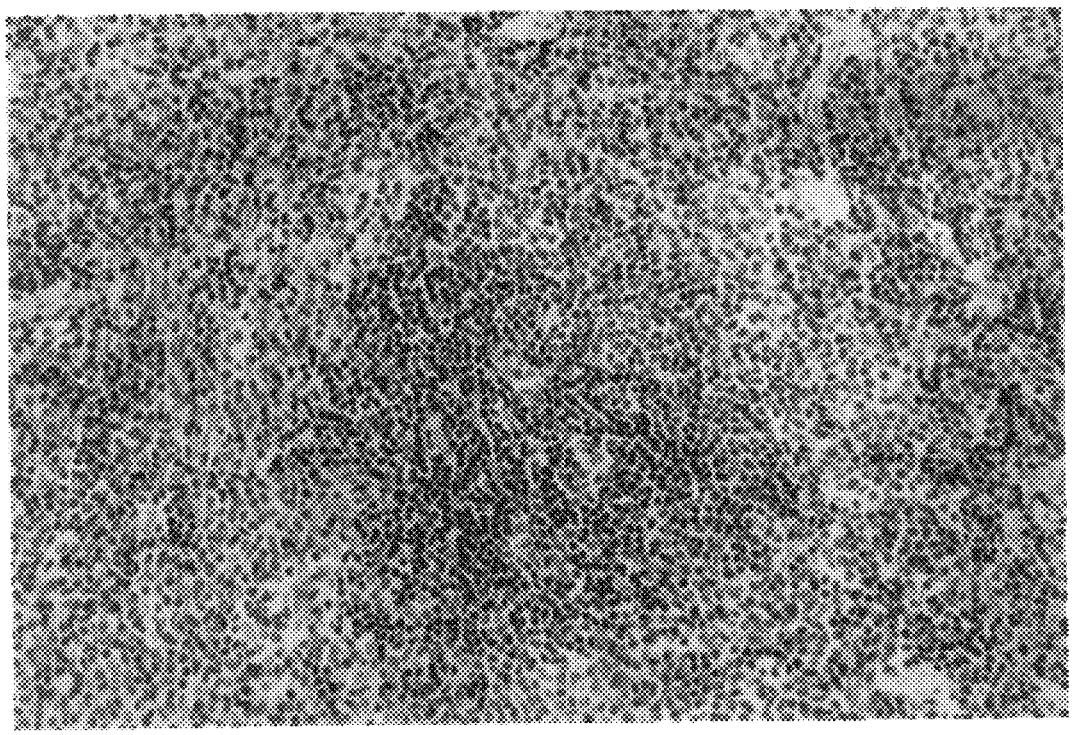
Figure 7C:
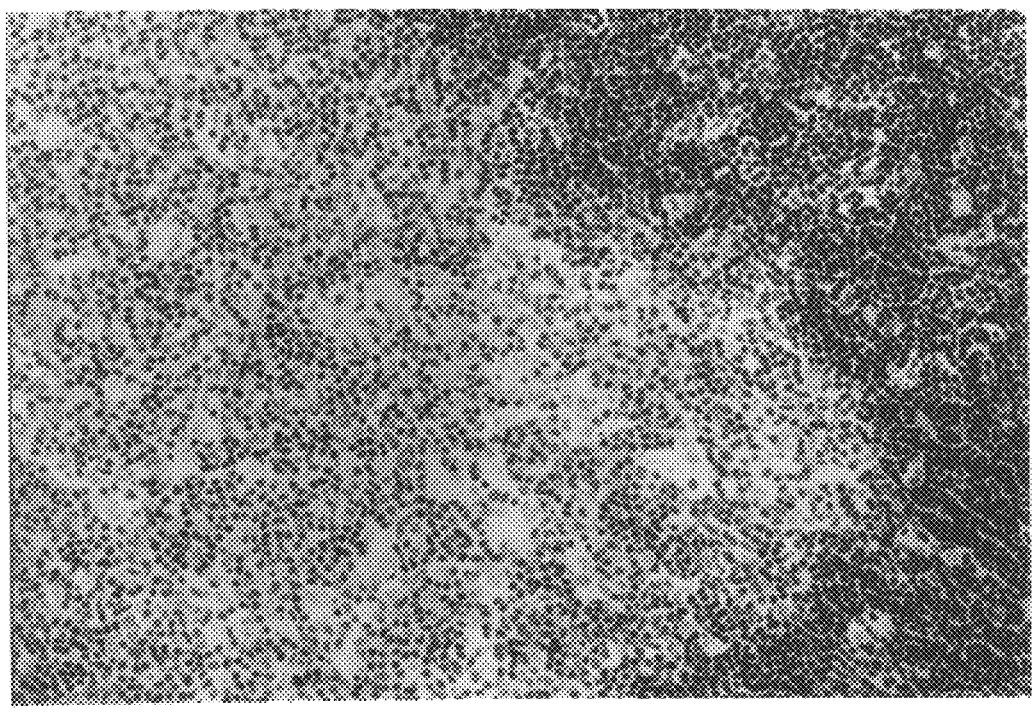
Figure 7D:
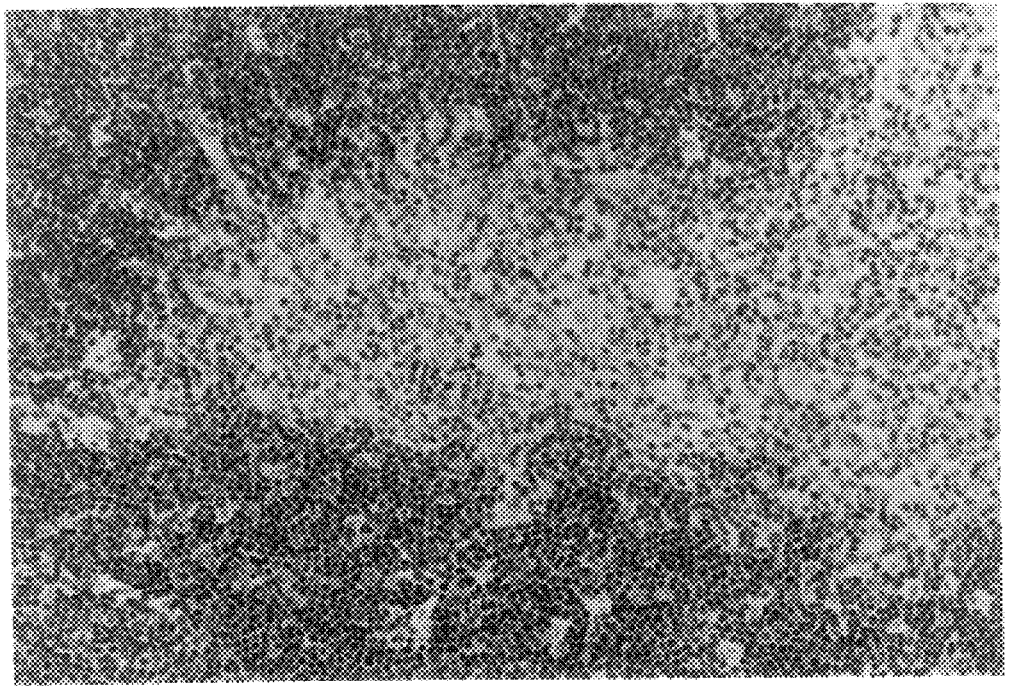
Figure 8A:
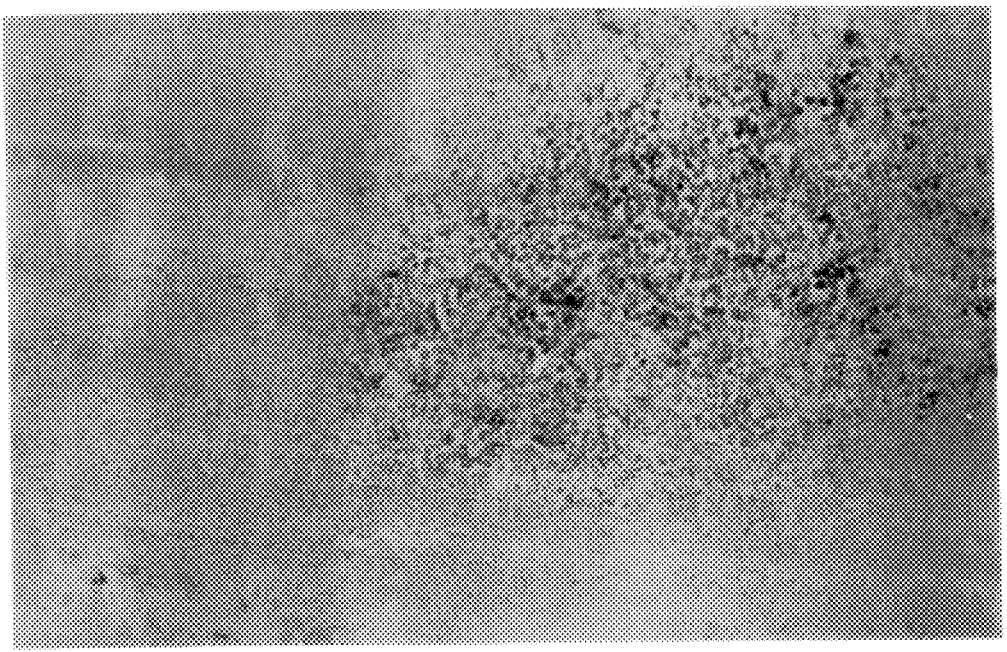
FIGS. 8(A–B) sets forth detection of thymocytes expressing HIV RNA by in situ hybridization. Sections of thymus from the JR-CSF transgenic mice were probed with anti-sense probe (A) and sense (B) probes as described herein.
Figure 8B:
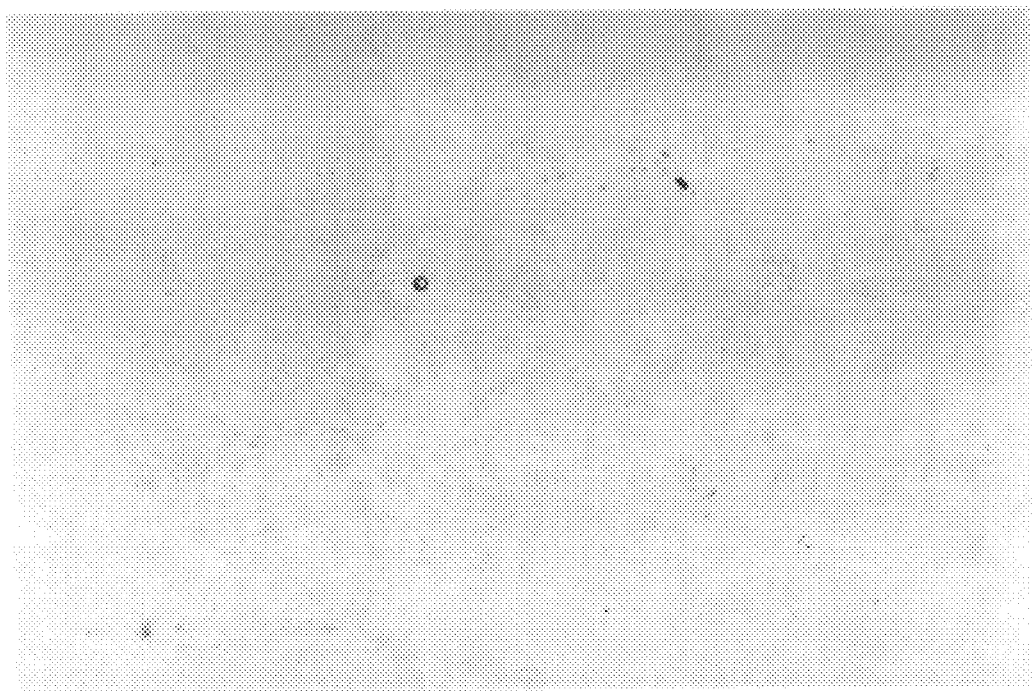

(iii) Histological and phenotypic analysis of lymphoid tissues: The effect of expression of the JR-CSF transgene on the architecture of their lymphoid tissues was evaluated by comparing the microscopic appearance of hematoxalin and eosin stained sections obtained from the JR-CSF transgenic mice (n=3 mice) to that of wild-type mice (n=3 mice). Sections of the spleen from both sets of mice showed preserved splenic architecture with well-developed splenic red and white pulp, and the white pulp of both sets of mice showed preserved marginal zones (FIGS. 7A and 7B). Germinal centers were observed in the white pulp of the spleen sections from all of the JR-CSF transgenic mice examined and contained large lymphoid cells, nuclear debris and tangible body macrophages while no germinal centers were seen in sections of spleens from the wild-type mice. The histology of the lymph nodes from both sets of mice showed preserved architecture with well defined follicular, cortical, and sinusoidal zones (FIGS. 7C and 7D). As seen in the splenic sections, secondary follicle fornation was observed in the lymph nodes from all of the JR-CSF transgenic mice but not in the lymph nodes from the wild-type mice. There was no significant difference between the histology of the thymus from the wild-type and JRCSF transgenic mice with both mice displaying well developed and sharply demarcated cortical and medullary zones (FIGS. 7E and 7F). The thymic tissue from the JR-CSF transgenic mice was further evaluated for evidence for active transcription of the transgene by in situ hybridization. As shown in FIG. 8, hybridization using the gag antisense probe on paraffin sections of the thymus shows markedly increased staining of thymocytes in a distribution suggestive of hybridization to thymocytes in the medullary zone. No staining of thymocytes in either cortical or medullary zones was observed after hybridization with the gag sense probe.

Figure 9:
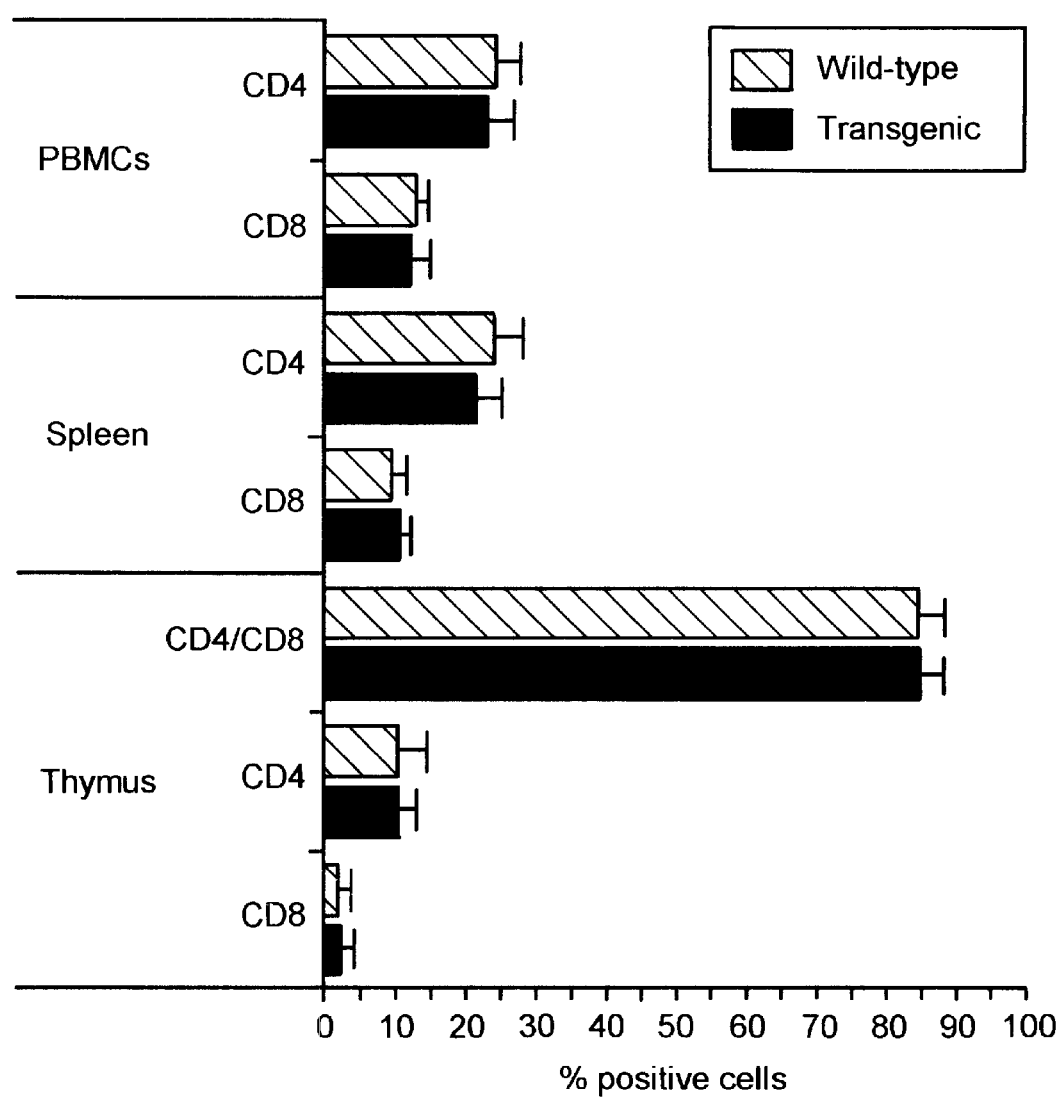
FIG. 9 sets forth analysis of T cell subsets in the peripheral blood, spleen and thymus of the JR-CSF transgenic mice. Mononuclear cells obtained from the blood, spleen and thymus of either JR-CSF transgenic mice (n=7, 4 and 3, respectively) or wild-type mice (n=3, 4 and 3, respectively) were analyzed by flow cytometry. The mean percentage of cells within the lymphocyte gates expressing CD4 alone, CD8 alone or CD4 and CD8 of the analyzed mice ±SEM is shown.
Figure 10:
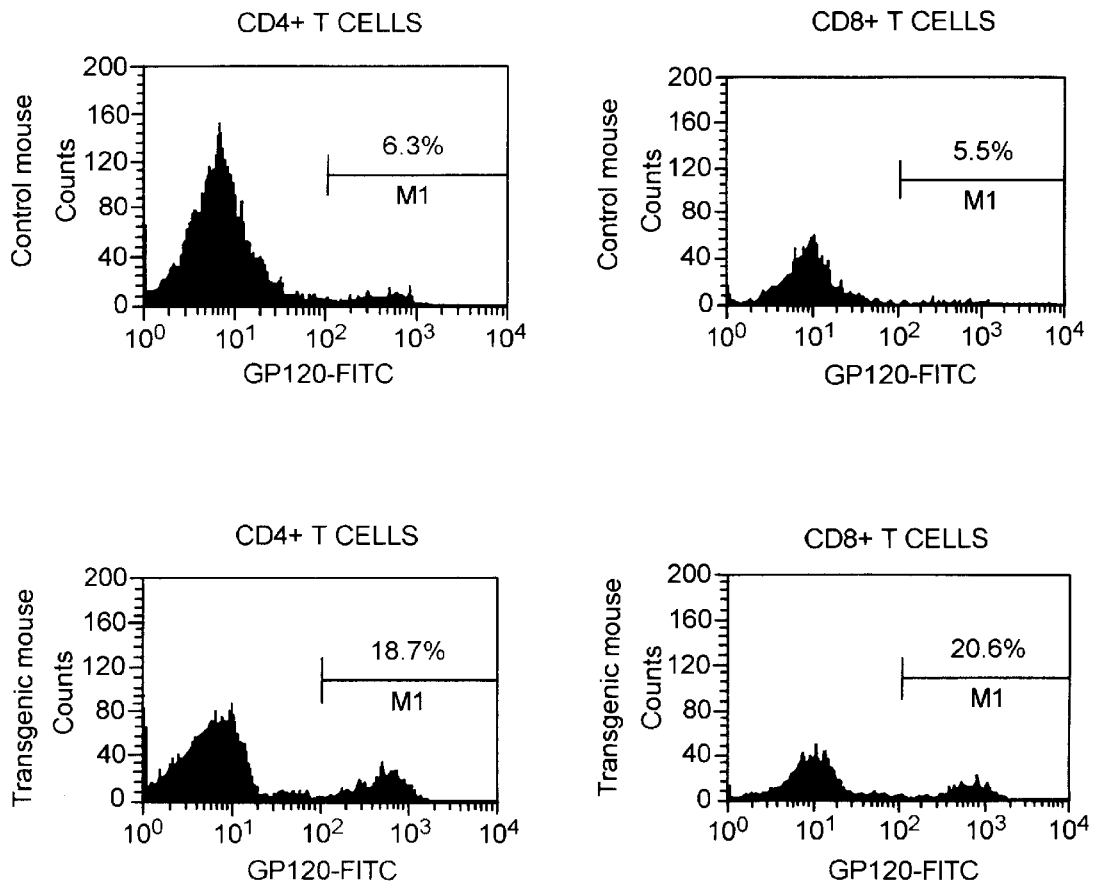
FIG. 10 sets forth detection of gp120 expression on T cells in JR-CSF transgenic mice. PBMCs from control wild-type mice (upper panels) or JR-CSF mice (lower panels) were analyzed for expression of gp120, CD4 and CD8 by three-color flow cytometry. The histograms for gp120 expression of cells that were CD4+ (left panels) or CD8+ (right panels) are shown and are representative of the analysis of 4 sets of control and JR-CSF transgenic mice.
Figure 11:
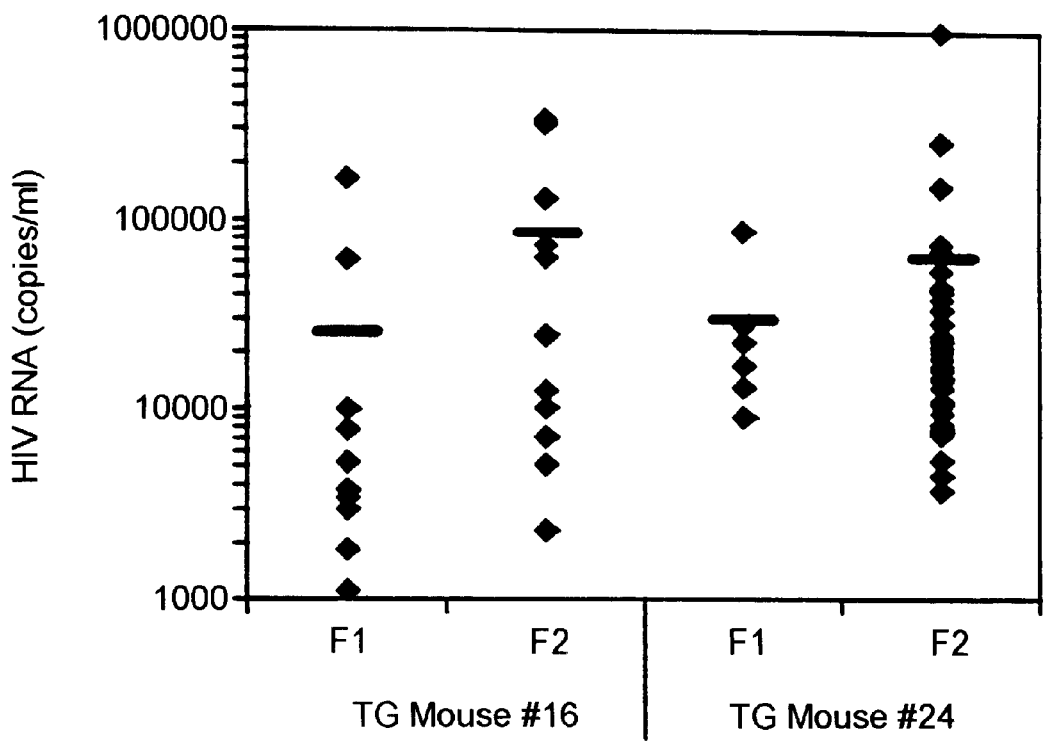
FIG. 11 JR-CSF mice display plasma viremia. The plasma HIV RNA level of the progeny of transgenic founder mice #16 (F1=10 mice, F2=11 mice) and #24 (F1=6 mice, F2=41 mice) was determined using the Roche AMPLICOR HIV-7 MONITOR™ Kit. Each point represents the level of HIV RNA in the plasma from a single mouse.

The T cell subpopulations in the peripheral blood, spleen, and thymus of the JR-CSF mice and wild-type mice were evaluated by flow cytometry. The percentage of CD4+ and CD8+ T cells in the peripheral blood and spleen, and the percentage of CD4/CD8 double positive, CD4 single positive and CD8 single positive thymocytes in the thymus of the JR-CSF mice were comparable to those detected in the wild-type mice (FIG. 9). To determine whether T cells in the JR-CSF transgenic mice produced HIV-1, T cells in the peripheral blood were examined for surface expression of HIV-1 gp120 using flow cytometry. PBMCs from control and JR-CSF transgenic mice were stained with monoclonal antibody to gp120 and either antibody to CD4 or to CD8 and analyzed by two-color flow cytometry. As shown in FIG. 11, over 18% and 20% of the CD4+ and CD8+ T cells, respectively, in the peripheral blood of the JR-CSF transgenic stained for gp120 expression compared to less than 6.5% of the CD4+ and CD8+ cells in the peripheral blood of control mice. Taken together, these results indicated that there was evidence of productive infection of T cells in the JR-CSF transgenic mice and that there were no significant histological differences between the lymphoid tissues of the JR-CSF mice and wild-type mice.

(iv) Plasma virernia is present in mice transgenic for HIV-1$_{JR-CSF}$: HIV RNA assays are used to measure plasma viremia in HIV-infected individuals to monitor the effect of therapeutic interventions on HIV replication (Carpenter C. C., et al., *JAMA* 280:78–86, 1998). The inventors previously demonstrated that plasma HIV RNA levels can be measured in mice such as HIV-infected thy/liv-SCID-hu mice and used to evaluate the degree of HIV replication occurring in the mice (Pettoello-Mantovani, M., et al., *J. Infect. Dis.* 177:337–346, 1998). To evaluate the extent of viral production occurring in the JR-CSF transgenic mice, the inventors evaluated the plasma from the F1 generation of mice derived from founder #16 and #24 for the presence of HIV RNA using the Roche AMPLICOR HIV-1 MONITOR™ assay. High levels of HIV RNA were detected in the plasma of all of the F1 progeny—from founders #6 (n=10 mice) and #24 (n=6 mice) that were positive for transmission of the transgene (FIG. 11). The plasma HIV RNA levels extent ranged from 1,111 copies/mil to 164,784 copies/ml, which are comparable to the range of plasma viremia observed in HIV-1 infected individuals. Thus, the extent of HIV-1 production occurring in the transgenic mice could be evaluated by measurement of the magnitude of plasma viremia.

Figure 12A:
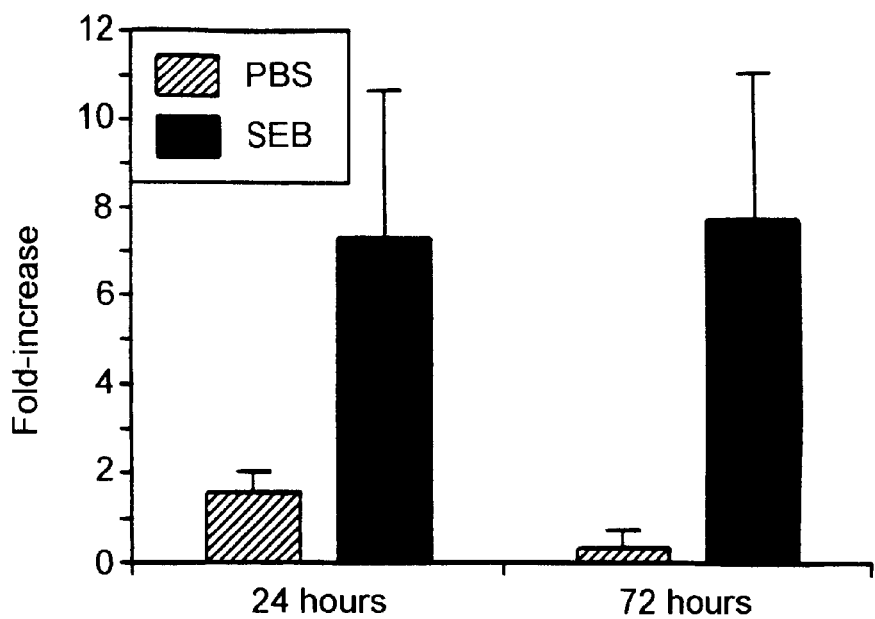
FIGS. 12(A–B) depicts increased production of HIV after stimulation of JR-CSF mice. (A) JR-CSF mice were treated with SEB (n=2 mice) or PBS (n=2 mice) and the plasma viral load was measured 24 hours and 72 hours later. The data are presented as the mean ±SE fold-increase of the plasma viral load of the mice treated with SEB or PBS. The fold-increase was calculated by dividing the plasma viral load measured at the indicated time with the baseline plasma viral load for each individual mouse. (B) JR-CSF mice were infected by i.v. injection of *M. tuberculosis* strain Erdman ($10^6$ pfu). The mean ±SEM levels of plasma HIV-1 RNA before infection and two weeks after infection are shown.

(v) Plasma HIV-1 RNA levels in the JR-CSF transgenic mice is increased by treatment with the superantigen SEB or by infection with *M. tuberculosis*. The plasma HIV-1 RNA levels of HIV-1-infected individuals increase after activation of their immune system by infection or vaccination (Stanley, et al., *Eur J Immunol* 23:2661–2666, 1993). The JR-CSF transgene is regulated by the HIV LTR. We demonstrated above (in FIG. 6C) that in vitro HIV-1 production by JR-CSF leukocytes was markedly increased by anti-CD3 stimulation which indicated that JR-CSF transgene expression was responsive to cellular stimulation. Consequently, we examined whether the JR-CSF mice would display a similar in vivo response to immune stimulation whereby in vivo activation of JR-CSF mouse T cells would induce LTR-driven transcription of the HIV transgene and subsequently increase in vivo HIV-1 production. To activate a large subset of mouse T cells by in vivo stimulation, the mice were treated with Staphylococcus enterotoxin B (SEB), a superantigen that rapidly stimulates Vβ8+ T cells (Stanley, et al., *Eur J Immunol* 23:2661–2666, 1993). Because of the presence of plasma viremia in the JR-CSF transgenic mice, the effect of in vivo stimulation of T cells on their production of HIV-1 could be monitored by measuring changes induced in the level of plasma viremia. Therefore, the inventors examined whether they could increase LTR-driven tranrscription of the transgene in T cells by investigating the effect that treatment of the mice with SEB had on their levels of plasma HIV RNA. After baseline plasma levels of HIV RNA in the transgenic mice were measured, the mice were injected either with SEB (50 μg) or with an equal volume of PBS. The mice were then bled 24 and 72 hours later and the plasma HIV RNA levels were determined (FIG. 12A). As shown in FIG. 12A, there was a rapid increase in the levels of plasma HIV RNA 24 hours after stimulation with SEB that was still present 72 hours after stimulation. In contrast, no increases of plasma HIV RNA levels were observed in the JR-CSF mice that were injected with PBS.

Figure 12B:
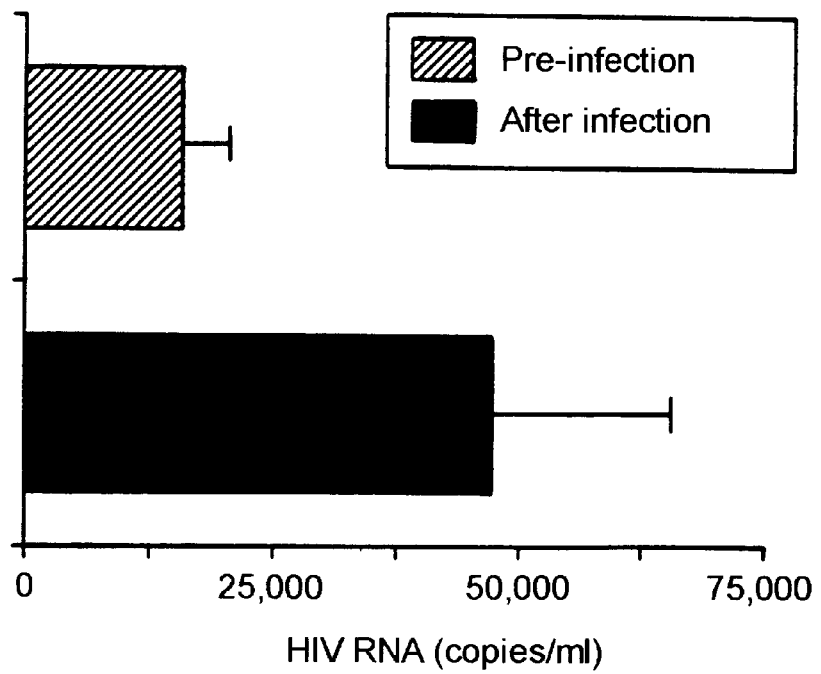

To determine whether HIV-1 production by the JR-CSF mice is increased by infection with an AIDS-associated pathogen, we examined the effect of *M. tuberculosis* infection on the plasma HIV RNA levels in JR-CSF mice. The JR-CSF mice (n=3 mice) were bled before infection to determine the baseline level of plasma HIV RNA and then bled again two weeks after infection with *M. tuberculosis*. As shown in FIG. 12B, *M. tuberculosis* infection of the mice induced a three-fold increase in the agnitude of plasma HIV RNA levels in the JR-CSF mice. Thus, production of HIV-1 by T cells in the JR-CSF transgenic mice could be modulated by in vivo stimulation or by infection with a pathogen that infected HIV-1-infected individuals.

Figure 13:
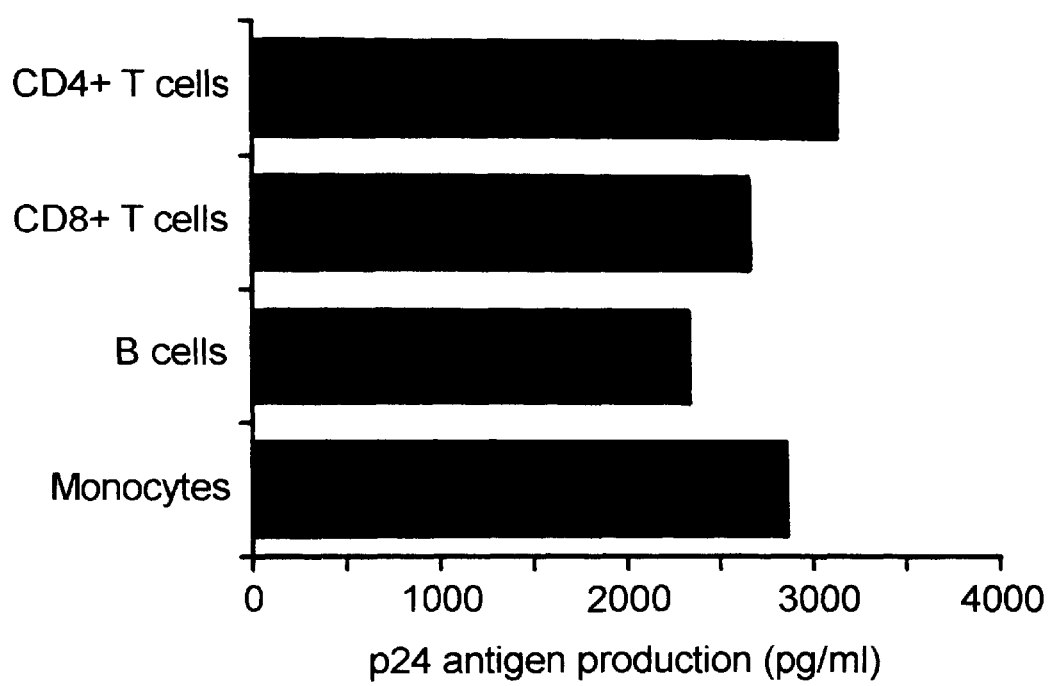
FIG. 13 illustrates production of HIV-1 by JR-CSF subsets. Highly purified CD4+ T cells, CD8 + T cells, B cells and monocytes from the JR-CSF mice were cocultured with PHA-activated human PBMCs and 2 weeks later an aliquot of the supernatant was assayed for the p24 antigen concentration.

(vi) HIV-1 is produced by T cells, B cells and monocytes in JR-CSF mice. To delineate which cells from the JR-CSF mice produced infectious HIV-1, highly purified JR-CSF mouse CD4+ and CD8+ T cells, B cells and monocytes isolated by magnetic bead separation were cocultured with activated human PBMCs. As shown in FIG. 8, productive HIV-1 infection occurred after coculture of highly purified CD4+ T cells, CD8+ T cells, B cells and monocytes with activated human donor PBMCs. To determine the in vivo contribution of cells other than T cells and B cells to the production of HIV-1 by the JR-CSF transgenic mice, we used a genetic approach. The JR-CSF transgenic mice were crossed with T and B cell-deficient SCID mice and we identified progeny JR-CSF transgenic mice homozygous for the SCID mutation and therefore deficient in T cells and B cells. The mice were bled and the plasma HIV RNA levels of the JR-CSF transgenic mice homozygous for the SCID mutation were compared to those of JR-CSF littermates populated with normal levels of T cells and B cells. As shown in FIG. 13, JR-CSF transgenic mice homozygous for the SCID mutation and lacking T cells and B cells had a mean level of 156,324 copies/ml of HIV-1 RNA compared to mean levels of 220,348 copies/ml in litterrnates heterozygous for the SCID mutation. Thus, HIV-1 present in the JR-CSF transgenic mice is produced by T cells, B cells, monocytes and possibly other cells.

Discussion

The previous studies describing mice transgenic for proviral DNA were performed using mice constructed with the NL4-3 provirus, but there are several reasons why this may not have been the optimum provirus to generate transgenic mice as a model to study in vivo HIV-1 function. First, the NL4-3 provirus was produced by fusing the 5' and 3' halves of 2 different T-cell tropic viruses, NY5 and LAV (Adachi A., et al., *J. Virol.* 59:284–291, 1986), and the behavior of such an artificial construct may differ from that of an unmanipulated provirus. Second, one of the isolates used to generate the construct, LAV, was a laboratory-adapted isolate whose function may differ from that of HIV-1 present in infected individuals due to alterations in HIV-1 behavior introduced during passage in cell lines (Groenink M., et al., *J. Virol.* 69:523–527, 1995). Third, the physiological relevance of transgenic models for studying transmission and behavior of HIV-1 would be increased by constructing the transgenic mice with a provirus derived from a direct patient isolate that was M-tropic, because M-tropic isolates are crucial in the initiation of infection, and predominate during the early stages of HIV infection (Hanna Z., et al., *J. Virol.* 72:121–132, 1998).

To develop a transgenic model using an strain more commonly isolated from HIV-infected individuals early in the course of disease, a full-length proviral construct was used derived from a M-tropic strain cloned soon after its isolation from an HIV-1-infected patient. The infectious proviral clone the inventors used to construct the transgenic mice, PYK-JRCSF, was isolated from the PBMCs of a HIV-infected individual after 11 days of culture with activated PBMCs (Koyanagi Y., et al., *Science* 236:819–822, 1987; Cann A. J., *J. Virol.* 64:4735–4742, 1990). In contrast to the T-cell tropic strain, HIV-1$_{NL}$4-3 encoded by the NL4-3 provirus that infects many established T-cell lines as well as peripheral blood lymphocytes, the primary M-tropic isolate encoded for by the PYK-JRCSF vector infects only peripheral blood lymphocytes and is unable to infect T-cell lines (Cann A. J., *J. Virol.* 64:4735–4742, 1990).

Leukocytes from 2 independent mouse lines transgenic for a full length, infectious provirus construct, PYK$_{JR-CSF}$, produced infectious virus and their plasma contained high levels of HIV RNA. This indicated that these JR-CSF transgenic mice were producing high levels of HIV-1. The majority of HIV-1 transgenic mouse lines that had been constructed using the NL4-3 provirus displayed a dramatic phenotype. The progeny of one line of transgenic mice constructed with the complete NL4-3 infectious provirus displayed epidermal hyperplasia, lymphadenopathy, growth retardation and early death (Leonard J. M., et al., *Science* 242:1665–1670, 1988). Although not capable of producing virions, transgenic mice generated with a gag-pol deletion mutant of the NL4-3 provirus exhibited cachexia, growth retardation, thymic hypoplasia and early death (Santoro T. J., et al., *Virology* 201:147–151, 1994). The transgenic mice produced with the NL4-3 provirus controlled by the murine leukemia virus promoter developed progressive myopathy,. weight loss, cachexia and periorbital celluhlitis (Dickie, P., et al., *J. Acquir. Immune Defic. Syndr. Hum. Retrovirol.* 13:101–116, 1996). When the NL4-3 provirus was placed under the control of the CD4 gene promoter/enhancer, the transgenic mice generated with this construct developed muscle wasting, severe atrophy of the lymphoid organs, tubulointerstidal nephritis, cachexia and early death (Hanna Z., et al., *J. Virol.* 72:121–132, 1998).

In marked contrast, none of these manifestations were observed in either founder mouse #16, founder mouse #24 or in any of their progeny. It is possible that this difference is related to the construction of the transgenic mice with a provirus derived from a CCR5-restricted M-tropic isolate instead of the CXCR4-restricted T-cell line tropic strain used in previous studies. Because of the sequence homology between human CXCR4 and mouse CXCR4, mouse CXCR4 can bind to human SDF-1 and induce signal transduction (Sawada S., et al.,. *J. Exp. Med.* 187:1439–1449, 1998), as well as function as a coreceptor with human CD4 to bind to T cell line-tropic env proteins and mediate cell infection (Tachibana, K., et al., *J. Exp. Med.* 185:1865–1870, 1997). Therefore it is possible that gp120 produced by the T-tropic NL4-3 provirus isolate could interfere with the interaction between CXCR4 and SDF-1 in the transgenic mice.

This may have important ramifications on the development of the transgenic mice because binding of SDF-1 to CXCR4 is crucial for normal mouse maturation as evidenced by the lethal phenotype observed in mice where the SDF-1 or the CXCR4 genes were disrupted by gene targeting (Zou Y. R., et al., *Nature* 393:595–599, 1998; Tachibana, K., et al., *Nature* 393:591–594, 1998; Nagasawa, T., et al., *Nature* 382:635–638, 1996). Thus, an intriguing possibility is that some of the phenotypes seen in the transgenic mice produced using the NL4-3 provirus may have been due to interference of the CXCR4-restricted gp120 protein on the SDF-1 and CXCR4 interaction required for normal murine differentiation. Because gp120 produced by M-tropic HIV-1 does not bind to mouse CXCR4 or even mouse CCR5, this would not occur in the inventors' JR-CSF transgenic mice and therefore may account for the absence in these mice of the multi-organ manifestations that were observed in the NL4-3 provirus-based transgenic mice.

Although the block in viral entry displayed by mouse cells is bypassed in mice transgenic for an HIV-1 provirus, replication of HIV-1 in mouse cells would still be decreased due to the reduced function of some HIV-1 regulatory genes in mouse cells (Chesebro, B., et al., *J. Virol.* 64:4553–4557, 1990). The activity of HIV-1 tat, the major positive regulator of HIV-1 gene expression, is markedly decreased in mouse cell lines due to the difference between the mouse and human homologues of cyclin T, a protein that interacts specifically with the transactivation domain of tat to facilitate its binding to the TAR region of the LTR (Winslow, B. J., et al., *J. Virol.* 67:2349–2354, 1993; Wei, P., et al., *Cell* 92:451–462, 1998). The function of another HIV-1 regulatory protein, Rev, which facilitates transport of incompletely spliced HIV-1 mRNAs from the nucleus into the cytoplasm, is also markedly diminished in mouse fibroblast cell lines (Winslow, B. J., et al., *J. Virol.* 67:2349–2354, 1993; Trono, D., et al., *EMBO* 9:4155–4160, 1990). The production of high levels of HIV-1 in the inventors' JR-CSF transgenic mice indicated that these blocks are not absolute and can be overcome by alternative pathways. For example, tat may induce activation of the LTR in the mice in a TAR-independent fashion and thereby bypass their cyclin T deficiency by using an alternate mechanism whereby tat interacts with the NF-KB binding domain of the LTR (Taylor J P, et al., *EMBO* 11:3395–3403, 1992). It is also possible that although tat and Rev activity is restricted in some mouse tissues such as fibroblasts, it may be functional in other mouse tissues such as lymphoid cells. For example, substantial tat-mediated trans-activation mediated by interaction between tat and TAR was detected in a mouse macrophage line, RAW264 (Murphey, K. M., et al., *J. Virol.* 67, 6956–6964, 1993), and functional Rev activity was observed in a murine T cell hybridoma (Newstein, M. E., et al., *J. Virol.* 64:4565–4567, 1990). Thus, sufficient activity of these regulatory genes may occur in the leukocytes from the JR-CSF transgenic mice to permit them to produce high levels of infectious virus. As proteins that restrict HIV-1 replication in a species-specific manner to humans become identified, the inventors would construct transgenic mice expressing the genes and cross them with the hu-CD4/CCRS and JR-CSF mice.

In contrast to the founder mice generated using the NL4-3 construct where HIV-1 could not be isolated by coculture (Leonard, et al., *Science* 242:1665, 1988), HIV-1 was readily cocultured from the PBMCs isolated from two of the JR-CSF transgenic founder mice, #16 and #24. Because the primary regulator of viral replication is the LTR, it is possible that the LTR from the HIV-1$_{JR-CSF}$ isolate may be better expressed in mouse cells than the LTR from the HIV-1$_{NL4-3}$ isolate. This was suggested by the inventors' observation (noted above) of the increased capacity of HIV-1$_{JR-CSF}$ to infect splenocytes from mice transgenic for human CD4 and CCR5. Divergent behavior of LTRs derived from different HIV-1 isolates was demonstrated in transgenic mice that exhibited central nervous system-expression of a reporter transgene driven by the LTR from HIV-1$_{JR-CSF}$ but not of a reporter transgene driven by the LTR from HIV-1$_{HIB/LAV}$ (Corboy J. R., et al., *Science* 258:1804–1808, 1992). The differential expression of LTRs from HIV-1$_{JR-CSF}$ and HIV-1$_{HIB/LAV}$ in mice may be related to their significant sequence variation which included substitutions in transcription factor binding sites that alter the NF-AT and LEF-1 binding sites (Corboy J. R., et al., *J. Neurovirol.* 3:331–341, 1997). The biological implications of other sequence variations-was indicated by the observation of functional binding of Jun and Fos to an AP-1 region in the LTR of HIV-1$_{JR-CSF}$ but not to the corresponding region in the HIV-1$_{LAI}$ LTR (Canonne-Hergaux, F., et al., *J. Virol.* 69:6634–6642, 1995).

It was postulated that the ability to measure plasma viremia in the JR-CSF transgenic mice would permit evaluation of the effects of various factors on the in vivo production of HIV-1 and demonstrated that treatment of the mice with SEB markedly increased the viral load present in the mice. Since SEB specifically stimulates Vβ8+ T cells (Baschieri, S., et al., *Eur. J. Immunol.* 23:2661–2666, 1993), the rapid rise in plasma HIV RNA levels detectable 24 hours after treatment suggested that activated T cells were the source of the increased plasma HIV RNA. Previous studies reported that within hours after the administration of SEB to mice, increased expression of TNF, IL-2 and IFN-γ mRNA and protein were detectable in their lymph nodes (Litton M. J., et al:, *J. Immunol. Methods* 175:47–58, 1994) and elevated serum levels of TNF and IL-2 were present in their serum (Miethke, T., et al., *J. Exp. Med.* 175:91–98, 1992). The increased plasma HIV levels in the SEB-treated JR-CSF transgenic mice was most likely due to the production of HIV by the mouse T cells that was induced by activation of the LTR after stimulation of the T cell receptor with SEB. Because TNF can induce the production of HIV from latently infected T cell clones (Duh E. J., et al., *Proc. Natl. Acad. Sci. USA* 86:5974–5978, 1989), it is possible that TNF produced in response to SEB may also have contributed to the increased HIV-1 observed in the SEB-stimulated JR-CSF transgenic mice. Infection of the mice with M. tuberculosis also increased plasma viremia. It is possible that TNF-α production induced by infection of the mice with *M. tuberculosis* (Hemandez-Pando, et al., *Immunology*, 90:607–17, 1997) stimulated HIV-1 production by infected cells as described (Poli, et al., *Proc. Natl. Acad. Sci., USA,* 87:782–5, 1990). The observation that viral production in these transgenic mice can be modulated by external treatments and monitored by measuring plasma virus levels should make these transgenic mice an extremely useful tool for evaluating the in vivo effect of different interventions on HIV-1 production.

C) hu-CD4/CCR5 Mice

Hu-CD4/CCR5 TG mice were crossed with JR-CSF TG mice to obtain mice heterozygous for expression of human CD4/CCR5 and the JR-CSF provirus. In these mice, one transgene encodes the production of virus while the other transgene encodes the expression of receptors that make the mouse cells sensitive to in vivo reinfection by the HIV-1 produced by the transgene. In addition, because the HIV-1 proteins are expressed in utero (evidenced by the development of plasma viremia in wild-type mothers bred to JR-CSF TG mice fathers), the JR-CSF TG mice and hu-CD4/CCR5/JRCSF TG mice are tolerant of HIV-1 and do not develop an HIV-1 specific immune response.

Figure 14:
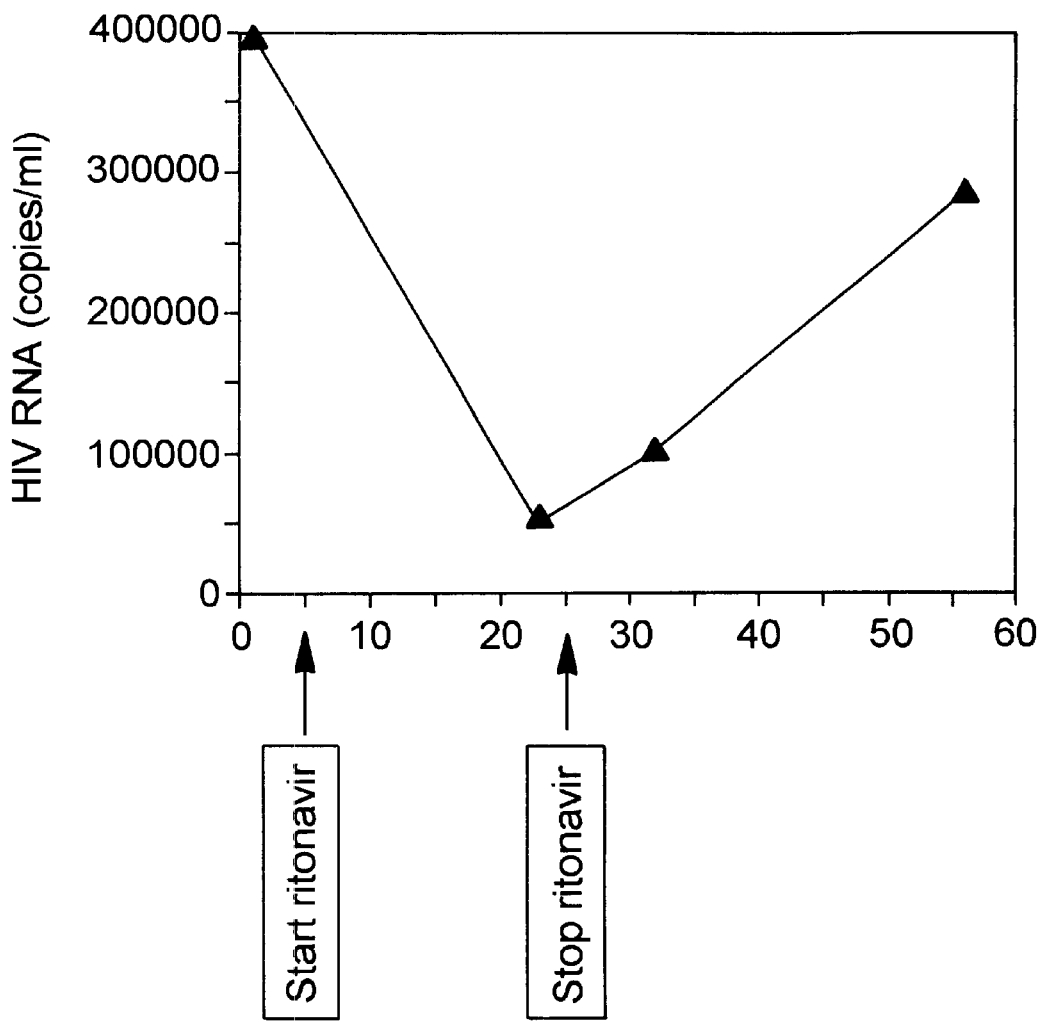
FIG. 14 is a graph depicting the effect of the protease inhibitor ritonavir on plasma viremia in hu-CD4/CCR5/JR-CSF transgenic mice.

Two lines of evidence suggest productive infection in the hu-CD4/CCR5/JRCSF TG mice. First, the mean plasma viral levels in the hu-CD4/CCR5/JRCSF TG mice are higher that in the JR-CSF TG mice. The second method takes advantage of the potent effect of protease inhibitors on blocking the production of infectious virus. HIV-1 infected cells treated with protease inhibitors will continue to produce virus but because the protease inhibitor is preventing post-translational modifications, the virus produced is not infectious and, by preventing infection of new cells, ultimately results in a dramatic drop in plasma HIV RNA levels. The inventors postulated that since secondary infection does not contribute to the viral load in JR-CSF TG mice, treatment with a protease inhibitor would not affect their plasma HIV RNA levels. In contrast, if secondary infection were occurring in the hu-CD4/CCR5/JRCSF TG mice, then treatment with a protease inhibitor would lower the plasma HIV RNA levels to the level that is constitutively produced by the JRCSF transgene. As predicted, after treatment of JR-CSF TG mice with a protease inhibitor, plasma viremia did not decrease and actually went up. In contrast, the plasma HIV RNA levels markedly decreased in the hu-CD4/CCR5/JRCSF TG mice after treatment with the protease inhibitor, and went back up after the protease inhibitor was stopped (see FIG. 14). This indicated that a significant proportion of the viral load in the hu-CD4/CCR5/JRCSF TG mice was due to the contribution of virus produced by secondarily infected mouse cells. Thus, these mice provide a self-contained system wherein factors that interfere with HIV-1 infection at any stage of the replication cycle can be studied.

Conclusion

HIV entry into human cells is mediated by CD4 acting in concert with one of several members of the chemokine receptor superfamily such as CCR5. Expression of human CD4 transgene alone does not render mice susceptible to HIV infection due to structural differences between human and mouse CCR5. This major barrier preventing HIV-1 infection of mouse cells, was overcome by the production of transgenic mice where human CD4 and CCR5 were expressed by mouse T cells (hu-CD4/CCR5 TG mice). Peripheral blood mononuclear cells and splenocytes isolated from these mice expressed human CD4 and CCR5 and were infectible with selected M-tropic HIV isolates. After in vivo inoculation, HIV-infected cells were detected by DNA PCR in the spleen and lymph nodes of these transgenic mice, but HIV could not be cultured from these cells. This indicated that although transgenic expression of human CD4 and CCR5 permitted entry of HIV into the mouse cells, despite repeated inoculations with high doses of HIV-1 significant HIV infection was prevented by other blocks to HIV replication present in mouse cells. In addition, these mice developed an HIV-specific immune response that was rapidly eliminating HIV infected cells. This significantly limited the usefulness of this model for studying HIV-1 infection or infection by other receptor mediated human-specific pathogens.

To circumvent this limitation, mice were developed that are transgenic for an infectious HIV-1 provirus. The restricted capacity of various HIV-1 isolates to infect monocytes and T cell lines permitted them to be characterized as either monocyte-tropic or T-cell line tropic, with monocyte-tropic isolates able to infect monocytes/macrophages but not T cell lines and T-cell line tropic isolates capable of infecting T cell lines but not monocytes. The observation that in order to penetrate into cells, HIV-1 must interact with a second receptor such as CXCR4 or CCR5 after binding to CD4, clarified the basis for the divergent cellular tropisms exhibited by different isolates of HIV with monocyte-tropic isolates utilizing CCR5 as a coreceptor and T-cell line tropic isolates using CXCR4 as a coreceptor. Two prior efforts at generation of mice transgenic for an infectious provirus used a molecular hybrid construct, NL4-3 that encoded a T-tropic isolate. These mice displayed low to undetectable levels of viral expression and were not useful in studying any aspects of HIV-1 replication. Because M-tropic isolates play a crucial role in the establishment of disease, the inventors created the first mouse lines transgenic for an infectious M-tropic provirus. A high degree of viral replication occurred in two of these independent transgenic mouse lines containing the full length HIV-1$_{JR-CSF}$ (JR-CSF TG mice) as evidenced by the isolation of infectious virus by coculture from their PBMCs and the presence of high levels of HIV RNA in their plasma comparable to that observed in HIV-1-infected individuals. However, the HIV-1 produced in this mouse cannot re-infect cells in these mice because of the inability of HIV-1 to enter into mouse cells.

hu-CD4/CCR5 TG mice were crossed with JR-CSF TG mice to obtain mice heterozygous for expression of human CD4/CCR5 and the JR-CSF provirus. In these mice, one transgene encodes the production of virus while the other transgene encodes the expression of receptors that make the mouse cells sensitive to in vivo reinfection by the HIV-1 produced by the transgene. In addition, because the HIV-1 proteins are expressed in utero (evidenced by the development of plasma viremia in wild-type mothers bred to JR-CSF TG mice fathers), the JR-CSF TG mice and hu-CD4/CCR5/JRCSF TG mice are tolerant of HIV-1 and do not develop an HIV-1 specific immune response. Thus, this approach of constructing a self-contained system for studying species-restricted pathogens by crossing (a) mice transgenic for a factor such as a receptor that grants susceptibility to infection by a pathogen they had previously been resistant to with (b) mice transgenic for the pathogen genome, thereby producing the pathogen, should prove to be a useful and unique model for the study of therapeutic interventions. This concept was demonstrated with the CD4/CCR5/JR-CSF transgenic mice using HIV-1 as the species-restricted pathogen. These particular mice should.prove useful for the screening of compounds effective to inhibit HIV infection.

Although the invention herein has been described with reference to particular embodiments, it is to be understood that these embodiments are merely illustrative of the various aspects of the invention. Thus, it is to be understood that numerous modifications may be made in the illustrative embodiments and other arrangements may be devised without departing from the spirit and scope of the invention.

What is claimed is:

1. A transgenic mouse whose genome comprises human CD4, human CCR5, and HIV-1 said transgenes, wherein the transgenes are expressed and HIV-1 replicates in at least splenocytes of transgenic mouse, and wherein the HIV-1 transgene encodes a monocyte-tropic HIV isolate.

2. A method for screening an agent for the ability to inhibit replication of HIV-1, comprising the steps of: (a) administering the agent to be screened to the transgenic mouse of claim 1; and (b) analyzing the effect of the administered agent on levels of HIV-1 replication in the transgenic mouse.

* * * * *

UNITED STATES PATENT AND TRADEMARK OFFICE
CERTIFICATE OF CORRECTION

PATENT NO. : 6,563,014 B2
DATED : May 13, 2003
INVENTOR(S) : Harris Goldstein and Jessie Browning Paul It is certified that error appears in the above-identified patent and that said Letters Patent is hereby corrected as shown below:

<u>Title page, Item [54], and Column 1, lines 1 and 2,</u>
The Title should read as the following:
-- A TRANSGENIC MOUSE THAT SUPPORTS HIV-1 REPLICATION IN SPLENOCYTES --

<u>Column 27,</u>
Lines 27-31, claim 1, should read:
Claim 1. A transgenic mouse whose genome comprises human CD4, human CCR5, and HIV-1 transgenes, wherein the transgenes are expressed and HIV-1 replicates in at least splenocytes of said transgenic mouse, and wherein the HIV-1 transgene encodes a monocyte-tropic HIV isolate.

Signed and Sealed this

Sixteenth Day of September, 2003

JAMES E. ROGAN
*Director of the United States Patent and Trademark Office*

SEQUENCE LISTING

```
<160> NUMBER OF SEQ ID NOS: 6

<210> SEQ ID NO 1
<211> LENGTH: 39
<212> TYPE: DNA
<213> ORGANISM: artificial sequence
<220> FEATURE:
<223> OTHER INFORMATION: primer

<400> SEQUENCE: 1
gtctgagtct gagtcggatc caacaagatg gattatcaa                39

<210> SEQ ID NO 2
<211> LENGTH: 39
<212> TYPE: DNA
<213> ORGANISM: artificial sequence
<220> FEATURE:
<223> OTHER INFORMATION: primer

<400> SEQUENCE: 2
gtctgagtct gagtcctcga gtccgtgtca caagcccac                39

<210> SEQ ID NO 3
<211> LENGTH: 24
<212> TYPE: DNA
<213> ORGANISM: artificial sequence
<220> FEATURE:
<223> OTHER INFORMATION: primer

<400> SEQUENCE: 3
gtggagttca aaatagacat cgtg                                24

<210> SEQ ID NO 4
<211> LENGTH: 27
<212> TYPE: DNA
<213> ORGANISM: artificial sequence
<220> FEATURE:
<223> OTHER INFORMATION: primer

<400> SEQUENCE: 4
```

```
cagcacccac accgccttct cccgctt                                      27

<210> SEQ ID NO 5
<211> LENGTH: 21
<212> TYPE: DNA
<213> ORGANISM: artificial sequence
<220> FEATURE:
<223> OTHER INFORMATION: primer

<400> SEQUENCE: 5
cacctgcagc tctcattttc c                                            21

<210> SEQ ID NO 6
<211> LENGTH: 20
<212> TYPE: DNA
<213> ORGANISM: artificial sequence
<220> FEATURE:
<223> OTHER INFORMATION: primer

<400> SEQUENCE: 6
ttgtagggag cccagaagag                                              20
```